United States Patent
Nagata et al.

(10) Patent No.: US 11,753,384 B2
(45) Date of Patent: *Sep. 12, 2023

(54) PRODUCTION METHOD FOR 5,5-DI-SUBSTITUTED-4,5-DIHYDROISOXAZOLE

(71) Applicant: KUMIAI CHEMICAL INDUSTRY CO., LTD., Tokyo (JP)

(72) Inventors: Toshihiro Nagata, Tokyo (JP); Daisuke Shikama, Tokyo (JP)

(73) Assignee: KUMIAI CHEMICAL INDUSTRY CO., LTD., Tokyo (JP)

( * ) Notice: Subject to any disclaimer, the term of this patent is extended or adjusted under 35 U.S.C. 154(b) by 393 days.

This patent is subject to a terminal disclaimer.

(21) Appl. No.: 17/049,128

(22) PCT Filed: Apr. 24, 2019

(86) PCT No.: PCT/JP2019/017459
§ 371 (c)(1),
(2) Date: Oct. 20, 2020

(87) PCT Pub. No.: WO2019/208643
PCT Pub. Date: Oct. 31, 2019

(65) Prior Publication Data
US 2021/0238150 A1   Aug. 5, 2021

(30) Foreign Application Priority Data
Apr. 27, 2018   (JP) .................. 2018-086679

(51) Int. Cl.
*C07D 261/04*   (2006.01)
*B01J 31/02*    (2006.01)

(52) U.S. Cl.
CPC ........ *C07D 261/04* (2013.01); *B01J 31/0232* (2013.01); *B01J 31/0237* (2013.01); *B01J 2231/348* (2013.01); *B01J 2531/002* (2013.01)

(58) Field of Classification Search
CPC .................................................. C07D 261/04
See application file for complete search history.

(56) References Cited

U.S. PATENT DOCUMENTS

| | | | |
|---|---|---|---|
| 6,541,642 B1 | 4/2003 | Yagihara et al. | |
| 2004/0110749 A1 | 6/2004 | Nakatani et al. | |
| 2010/0249424 A1 | 9/2010 | Annis et al. | |
| 2012/0238760 A1 | 9/2012 | Frassetto | |
| 2013/0225600 A1 | 8/2013 | Irlapati et al. | |

FOREIGN PATENT DOCUMENTS

| | | |
|---|---|---|
| CN | 102666503 A | 9/2012 |
| CN | 103228636 A | 7/2013 |
| CN | 107652245 A | 2/2018 |
| EP | 3725782 A1 | 10/2020 |
| JP | 2013-512202 A | 4/2013 |
| TW | 200914429 A | 4/2009 |
| WO | 00/58290 A1 | 10/2000 |
| WO | 02/062770 A1 | 8/2002 |
| WO | 2011/063843 A1 | 6/2011 |

OTHER PUBLICATIONS

"Synthesis and Reaction of Organic Compounds III", New Experimental Chemistry Course 14, Maruzen Inc., 1978, pp. 1325-1328, cited in ISR, w/English partial translation (10 pages).
Zhu et al., "TEMPO—Mediated Aliphatic C—H Oxidation with Oximes and Hydrazones", Organic Letters, 2013, vol. 15, No. 13, pp. 3214-3217, cited in ISR (4 pages).
Uncuta et al., "Hydration of 2-Isoxazoline Leading to a Stable 3,5,5-Trisubstituted 3-Isoxazolidinol-N-Acylated Derivatives and Ring-Chain Tautomerism Study", European Journal of Organic Chemistry, 2002, No. 12, pp. 1919-1924, cited in ISR (6 pages).
Pohjakallio et al., "A Versatile Entry to 3-Unsubstituted 2-Isoxazolines", Synlett, 2008, No. 6, pp. 827-830, cited in Specification (4 pages).
Pohjakallio et al., "Synthesis of 2-Isoxazolines: Enantioselective and Racemic Methods Based on Conjugate Additions of Oximes", Chem. Eur. J. 2010, vol. 16, pp. 11325-11339, cited in Specification (15 pages).

(Continued)

*Primary Examiner* — Shawquia Jackson
(74) *Attorney, Agent, or Firm* — WHDA, LLP

(57) ABSTRACT

The objective of the present invention is to provide a production method for a 4,5-dihydroisoxazole represented by formula (3), which is safe, industrially desirable, economical, and environmentally friendly.

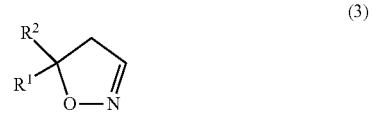

(3)

The present invention causes the compound of formula (1) to react with hydroxylamine in the presence of an acid catalyst to produce the compound of formula (3) through the reaction represented by the reaction equation.

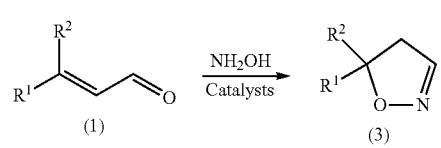

22 Claims, No Drawings

(56) References Cited

OTHER PUBLICATIONS

International Search Report dated Jul. 16, 2019, issued in counterpart International Application No. PCT/JP2019/017459 (2 pages).
Office Action dated Oct. 5, 2022, issued in counterpart TW application No. 108114335, with English translation. (17 pages).
Extended (Supplementary)European Search Report dated Oct. 27, 2021, issued in counterpart EP Application No. 19793641.2. (7 pages).
Office Action dated Mar. 25, 2023, issued in counterpart CN application No. 201980025644.7. (6 pages).

PRODUCTION METHOD FOR 5,5-DI-SUBSTITUTED-4,5-DIHYDROISOXAZOLE

TECHNICAL FIELD

The present invention relates to a process for producing a compound of a formula (3):

[Chemical Formula 1]

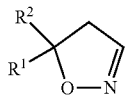

wherein, $R^1$ and $R^2$ are as described later, i.e., a 5,5-disubstituted-4,5-dihydroisoxazole. Herein, the compound of the formula (3) is also referred to as a 5,5-disubstituted-2-isoxazoline.

BACKGROUND ART 5,5-Disubstituted-4,5-dihydroisoxazoles of the formula (3) are useful as intermediates for the production of pharmaceuticals, agricultural chemicals, etc. WO 2002/062770 (Patent Document 1) discloses useful herbicides. Among them, pyroxasulfone is well known as a herbicide having excellent herbicidal activity.
Furthermore, JP 2013-512202 A (Patent Document 2) discloses that the 5,5-disubstituted-4,5-dihydroisoxazoles of the formula (3) are important intermediates for the herbicides described in Patent Document 1.
JP 2013-512202 A (Patent Document 2) discloses a process for producing 5,5-disubstituted-4,5-dihydroisoxazoles.
Scheme 2 of Patent Document 2:

[Chemical Formula 2]

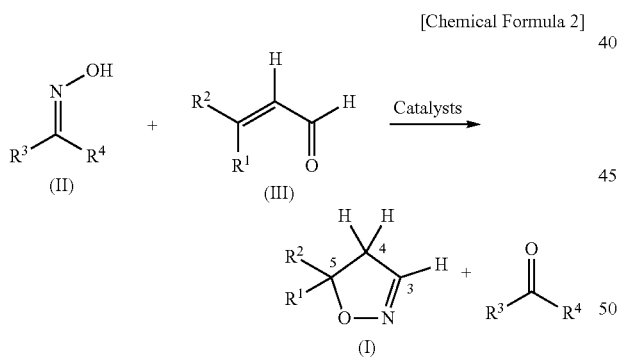

As shown in the above scheme, in the process described in Patent Document 2, an oxime of the formula (II) is reacted with a carbonyl compound of the formula (III) (a β-disubstituted-α,β-unsaturated aldehyde) in the presence of an acid catalyst or an acid-base catalyst, to obtain a 5,5-disubstituted-4,5-dihydroisoxazole of the formula (I).

Synlett 2008, No. 6, 827-830 (Non-Patent Document 1) and Chem. Eur. J. 2010, Vol. 16, 11325-11339 (Non-Patent Document 2) describe processes of producing a 4,5-dihydroisoxazole derivative by using a ketone oxime.

Due to the industrial importance of the compound of the formula (3), there is a desire for a process for producing the compound of the formula (3) which is more industrially preferable than the prior art.

CITATION LIST

Patent Document

Patent Document 1: WO 2002/062770 A1
Patent Document 2: JP 2013-512202 A

Non-Patent Document

Non-Patent Document 1: Synlett 2008, No. 6, 827-830
Non-Patent Document 2: Chem. Eur. J. 2010, Vol. 16, 11325-11339

SUMMARY OF INVENTION

Technical Problem

An object of the present invention is to provide an industrially preferable process for producing the compound of the above formula (3), i.e., the target 5,5-disubstituted-4,5-dihydroisoxazole.
Another object of the present invention is to provide a process for producing the target compound efficiently by a simple operation.

Solution to Problem

In view of the circumstances as described above, the present inventor has earnestly studied a process for producing a compound of the formula (3). As a result, the present inventor unexpectedly found that the above problems can be solved by providing the following processes for producing the compound of the formula (3). The present inventor has accomplished the present invention based on this finding.
That is, in one embodiment, the present invention is as follows.
[I-1] A process for producing a compound of the formula (3), which comprises reacting a compound of the formula (1) with hydroxylamine in the presence of a catalyst:

[Chemical Formula 3]

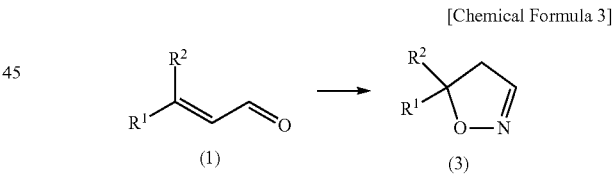

in the formula (3), $R^1$ and $R^2$ are each independently an optionally substituted (C1-C6)alkyl; an optionally substituted (C3-C6)cycloalkyl, an optionally substituted (C2-C6)alkenyl; an optionally substituted (C2-C6)alkynyl; an optionally substituted (C1-C6)alkoxy; or an optionally substituted phenyl; or
$R^1$ and $R^2$, together with the carbon atom to which they are attached form a 4- to 12-membered carbocyclic ring, wherein the formed ring is optionally substituted;
in the formula (1), $R^1$ and $R^2$ are as defined above.
[I-2] The process according to [I-1], wherein the reaction of the compound of the formula (1) with hydroxylamine is performed in the presence of water.
[I-3] The process according to [I-1], wherein the reaction of the compound of the formula (1) with hydroxylamine is performed in the presence of 50 mol % or more of water based on 1 mol of the compound of the formula (1).

[I-4] The process according to [I-1], wherein the reaction of the compound of the formula (1) with hydroxylamine is performed in the presence of 100 mol % or more of water based on 1 mol of the compound of the formula (1).
[I-5] The process according to [I-1], wherein the reaction of the compound of the formula (1) with hydroxylamine is performed in the presence of 150 mol % or more of water based on 1 mol of the compound of the formula (1).
[I-6] The process according to [I-1], wherein the reaction of the compound of the formula (1) with hydroxylamine is performed in the presence of 50 mol % to 6000 mol % of water based on 1 mol of the compound of the formula (1).
[I-7] The process according to [I-1], wherein the reaction of the compound of the formula (1) with hydroxylamine is performed in the presence of 50 mol % to 3000 mol % of water based on 1 mol of the compound of the formula (1).
[I-8] The process according to [I-1], wherein the reaction of the compound of the formula (1) with hydroxylamine is performed in the presence of 50 mol % to 1000 mol % of water based on 1 mol of the compound of the formula (1).
[I-9] The process according to [I-1], wherein the reaction of the compound of the formula (1) with hydroxylamine is performed in the presence of 100 mol % to 6000 mol % of water based on 1 mol of the compound of the formula (1).
[I-10] The process according to [I-1], wherein the reaction of the compound of the formula (1) with hydroxylamine is performed in the presence of 100 mol % to 3000 mol % of water based on 1 mol of the compound of the formula (1).
[I-11] The process according to [I-1], wherein the reaction of the compound of the formula (1) with hydroxylamine is performed in the presence of 100 mol % to 1500 mol % of water based on 1 mol of the compound of the formula (1).
[I-12] The process according to [I-1], wherein the reaction of the compound of the formula (1) with hydroxylamine is performed in the presence of 100 mol % to 1000 mol % of water based on 1 mol of the compound of the formula (1).
[I-13] The process according to [I-1], wherein the reaction of the compound of the formula (1) with hydroxylamine is performed in the presence of 100 mol % to 500 mol % of water based on 1 mol of the compound of the formula (1).
[I-14] The process according to [I-1], wherein the reaction of the compound of the formula (1) with hydroxylamine is performed in the presence of 150 mol % to 6000 mol % of water based on 1 mol of the compound of the formula (1).
[I-15] The process according to [I-1], wherein the reaction of the compound of the formula (1) with hydroxylamine is performed in the presence of 150 mol % to 3000 mol % of water based on 1 mol of the compound of the formula (1).
[I-16] The process according to [I-1], wherein the reaction of the compound of the formula (1) with hydroxylamine is performed in the presence of 150 mol % to 1000 mol % of water based on 1 mol of the compound of the formula (1).
[I-17] The process according to [I-1], wherein the reaction of the compound of the formula (1) with hydroxylamine is performed in the presence of 150 mol % to 400 mol % of water based on 1 mol of the compound of the formula (1).
[I-18] The process according to [I-1], wherein the reaction of the compound of the formula (1) with hydroxylamine is performed in the presence of 180 mol % to 6000 mol % of water based on 1 mol of the compound of the formula (1).
[I-19] The process according to [I-1], wherein the reaction of the compound of the formula (1) with hydroxylamine is performed in the presence of 180 mol % to 350 mol % of water based on 1 mol of the compound of the formula (1).
[I-20] The process according to any one of [I-1] to [I-19], wherein the catalyst is an acid catalyst.
[I-21] The process according to [I-20], wherein the acid catalyst is one or more (preferably one to three, more preferably one or two, even more preferably one) acid(s) selected from the group consisting of mineral acids, carboxylic acids, sulfonic acids, and phosphoric acids.
[I-22] The process according to [I-20], wherein the acid catalyst is one or more (preferably one to three, more preferably one or two, even more preferably one) acid(s) selected from the group consisting of mineral acids, carboxylic acids, and sulfonic acids.
[I-23] The process according to [I-20], wherein the acid catalyst is one or more (preferably one to three, more preferably one or two, even more preferably one) acid(s) selected from the group consisting of nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, and diphenyl phosphate.
[I-24] The process according to [I-20], wherein the acid catalyst is one or more (preferably one to three, more preferably one or two, even more preferably one) acid(s) selected from the group consisting of nitric acid, trifluoroacetic acid, trichloroacetic acid, maleic acid, maleic anhydride, benzenesulfonic acid, and p-toluenesulfonic acid.
[I-25] The process according to [I-20], wherein the acid catalyst is one or more (preferably one to three, more preferably one or two, even more preferably one) acid(s) selected from the group consisting of nitric acid, trifluoroacetic acid, maleic acid, and p-toluenesulfonic acid.
[I-26] The process according to [I-20], wherein the acid catalyst is one to three (preferably one or two, more preferably one) acid(s) selected from the group consisting of trifluoroacetic acid, maleic acid, and maleic anhydride.
[I-27] The process according to [I-20], wherein the acid catalyst is one or two (preferably one) acid(s) selected from the group consisting of trifluoroacetic acid and maleic acid.
[I-28] The process according to [I-20], wherein the acid catalyst is trifluoroacetic acid.
[I-29] The process according to any one of [I-20] to [I-28], wherein the amount of the acid catalyst used is 0.01 to 0.30 mol based on 1 mol of the compound of the formula (1).
[I-30] The process according to any one of [I-20] to [I-29], wherein the amount of the hydroxylamine is 0.9 to 1.1 mol based on 1 mol of the compound of the formula (1).
[I-31] The process according to any one of [I-20] to [I-29], wherein the amount of the hydroxylamine is 1.0 to 1.1 mol based on 1 mol of the compound of the formula (1).
[I-32] The process according to any one of [I-1] to [I-19], wherein the catalyst is an acid-base catalyst.
[I-33] The process according to [I-32], wherein the acid of the acid-base catalyst is one or more (preferably one to three, more preferably one or two, even more preferably one) acid(s) selected from the group consisting of mineral acids, carboxylic acids, sulfonic acid, and phosphoric acids.
[I-34] The process according to [I-32], wherein the acid of the acid-base catalyst is one or more (preferably one to three, more preferably one or two, even more preferably one) acid(s) selected from the group consisting of mineral acids, carboxylic acids, and sulfonic acids.
[I-35] The process according to [I-32], wherein the acid of the acid-base catalyst is one or more (preferably one to three, more preferably one or two, even more preferably one) acid(s) selected from the group consisting of nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, and diphenyl phosphate.

[I-36] The process according to [I-32], wherein the acid of the acid-base catalyst is one or more (preferably one to three, more preferably one or two, even more preferably one) acid(s) selected from the group consisting of nitric acid, trifluoroacetic acid, trichloroacetic acid, maleic acid, maleic anhydride, benzenesulfonic acid, and p-toluenesulfonic acid.

[I-37] The process according to [I-32], wherein the acid of the acid-base catalyst is one or more (preferably one to three, more preferably one or two, even more preferably one) acid(s) selected from the group consisting of nitric acid, trifluoroacetic acid, maleic acid, and p-toluenesulfonic acid.

[I-38] The process according to [I-32], wherein the acid of the acid-base catalyst is one to three (preferably one or two, more preferably one) acid(s) selected from the group consisting of trifluoroacetic acid, maleic acid, and maleic anhydride.

[I-39] The process according to [I-32], wherein the acid of the acid-base catalyst is one or two (preferably one) acid(s) selected from the group consisting of trifluoroacetic acid and maleic acid.

[I-40] The process according to [I-32], wherein the acid of the acid-base catalyst is trifluoroacetic acid.

[I-41] The process according to any one of [1-32] to [I-40], wherein the amount of the acid of the acid-base catalyst used is 0.005 to 0.10 mol based on 1 mol of the compound of the formula (1).

[I-42] The process according to any one of [I-32] to [I-41], wherein the base of the acid-base catalyst is one or more (preferably one to three, more preferably one or two, even more preferably one) secondary amine(s).

[I-43] The process according to any one of [I-32] to [I-41], wherein the base of the acid-base catalyst is one or more (preferably one to three, more preferably one or two, even more preferably one) base(s) selected from the group consisting of N-methylaniline, morpholine, and pyrrolidine.

[I-44] The process according to any one of [I-32] to [I-41], wherein the base of the acid-base catalyst is N-methylaniline.

[I-45] The process according to any one of [I-32] to [I-44], wherein the amount of the base of the acid-base catalyst used is 0.005 to 0.10 mol based on 1 mol of the compound of the formula (1).

[I-46] The process according to any one of [1-32] to [I-45], wherein the amount of the hydroxylamine is 0.90 mol or more and less than 1.00 mol based on 1 mol of the compound of the formula (1).

[I-47] The process according to any one of [I-32] to [I-45], wherein the amount of the hydroxylamine is 0.90 mol or more and 0.99 mol or less based on 1 mol of the compound of the formula (1).

[I-48] The process according to any one of [I-32] to [I-45], wherein the amount of the hydroxylamine is 0.90 mol to 0.98 mol based on 1 mol of the compound of the formula (1).

[I-49] The process according to any one of [I-1] to [I-48], wherein the hydroxylamine is a free hydroxylamine aqueous solution or a hydroxylamine salt.

[I-50] The process according to any one of [I-1] to [I-48], wherein the hydroxylamine is a free hydroxylamine aqueous solution, hydroxylamine hydrochloride, or hydroxylamine sulfate.

[I-51] The process according to any one of [I-1] to [I-48], wherein the hydroxylamine is a 45% to 55% hydroxylamine aqueous solution, hydroxylamine hydrochloride, or hydroxylamine sulfate.

[I-52] The process according to any one of [I-1] to [I-48], wherein the hydroxylamine is a 45% to 50% hydroxylamine aqueous solution, hydroxylamine hydrochloride, or hydroxylamine sulfate.

[I-53] The process according to any one of [I-1] to [I-48], wherein the hydroxylamine is a hydroxylamine salt, and the reaction is performed in the further presence of a neutralizing agent.

[I-54] The process according to any one of [I-1] to [I-48], wherein the hydroxylamine is hydroxylamine hydrochloride or hydroxylamine sulfate, and the reaction is performed in the further presence of a neutralizing agent.

[I-55] The process according to [1-53] or [I-54], wherein the neutralizing agent is sodium hydroxide, potassium hydroxide, sodium carbonate, potassium carbonate, sodium hydrogen carbonate, potassium hydrogen carbonate, or ammonia.

[I-56] The process according to [I-53] or [I-54], wherein the neutralizing agent is sodium hydroxide.

[I-57] The process according to any one of [I-1] to [I-56], wherein the reaction is performed in the presence of one or more (preferably one or two, more preferably one) solvent(s) selected from acetonitrile, toluene, xylene, chlorobenzene, dichlorobenzene, and dichloromethane, and a water solvent.

[I-58] The process according to any one of [I-1] to [I-56], wherein the reaction is performed in the presence of one or more (preferably one or two, more preferably one) solvent(s) selected from toluene, xylene, chlorobenzene, dichlorobenzene, and dichloromethane, and a water solvent.

[I-59] The process according to any one of [I-1] to [I-56], wherein the reaction is performed in the presence of one or more (preferably one or two, more preferably one) solvent(s) selected from acetonitrile and dichloromethane, and a water solvent.

[I-60] The process according to any one of [I-1] to [I-56], wherein the reaction is performed in the presence of a solvent composed of a combination of water and dichlorobenzene (i.e., a mixed solvent of water and dichlorobenzene).

[I-61] The process according to any one of [I-1] to [I-60], wherein the reaction is performed at 0° C. to 80° C.

[I-62] The process according to any one of [I-1] to [I-60], wherein the reaction is performed at 20° C. to 80° C.

[I-63] The process according to any one of [I-1] to [I-60], wherein the reaction is performed at 40° C. to 60° C.

[I-64] The process according to any one of [I-1] to [I-60], wherein the reaction is performed at 20° C. to 40° C.

[I-65] The process according to any one of [I-1] to [I-64], wherein $R^1$ and $R^2$ are each independently (C1-C6)alkyl; (C1-C6)haloalkyl; (C3-C6)cycloalkyl; (C2-C6)alkenyl; (C2-C6)alkynyl; (C1-C6)alkoxy; or phenyl optionally substituted with 1 to 5 substituents independently selected from halogen atoms, (C1-C4)alkyl, and (C1-C4)haloalkyl; or $R^1$ and $R^2$, together with the carbon atom to which they are attached form a 4- to 6-membered carbocyclic ring.

[I-66] The process according to any one of [I-1] to [I-64], wherein $R^1$ and $R^2$ are each independently (C1-C4)alkyl; (C1-C4)haloalkyl; (C3-C6)cycloalkyl; (C2-C4)alkenyl; (C2-C4)alkynyl; (C1-C4)alkoxy; or phenyl optionally substituted with 1 to 5 substituents independently selected from halogen atoms, (C1-C4)alkyl, and (C1-C4)haloalkyl; or $R^1$ and $R^2$, together with the carbon atom to which they are attached form a 4- to 6-membered carbocyclic ring.

[I-67] The process according to any one of [I-1] to [I-64], wherein $R^1$ and $R^2$ are each independently (C1-C4)alkyl or (C1-C4)haloalkyl.
[I-68] The process according to any one of [I-1] to [I-64], wherein $R^1$ and $R^2$ are each independently (C1-C4)alkyl.
[I-69] The process according to any one of [I-1] to [I-64], wherein $R^1$ and $R^2$ are methyl.
[I-70] The process according to any one of [I-1] to [I-64], wherein the compound of the formula (1) is prenal and the compound of the formula (3) is 5,5-dimethyl-4,5-dihydroisoxazole.

In another embodiment, the present invention is as follows.

[II-1] A process for producing a compound of the formula (3), which comprises reacting a compound of the formula (1) with hydroxylamine in the presence of a catalyst,

[Chemical Formula 100]

$$R^1\underset{(1)}{\overset{R^2}{\diagup\!\!\!\diagdown}}\!\!=\!\!\diagdown\!\!\diagup\text{O} \longrightarrow R^1\underset{(3)}{\overset{R^2}{\diagup\!\!\!\diagdown}}\!\!\diagdown_{\text{O}-\text{N}}$$

in the formula (3), $R^1$ and $R^2$ are each independently an optionally substituted (C1-C6)alkyl; an optionally substituted (C3-C6)cycloalkyl, an optionally substituted (C2-C6)alkenyl; an optionally substituted (C2-C6)alkynyl; an optionally substituted (C1-C6)alkoxy; or an optionally substituted phenyl; or $R^1$ and $R^2$, together with the carbon atom to which they are attached form a 4- to 12-membered carbocyclic ring, wherein the formed ring is optionally substituted;

in the formula (1), $R^1$ and $R^2$ are as defined above.

[II-2] The process according to [II-1], wherein the reaction of the compound of the formula (1) with hydroxylamine is performed in the presence of water.
[II-3] The process according to [II-1], wherein the reaction of the compound of the formula (1) with hydroxylamine is performed in the presence of 100 mol % or more of water based on 1 mol of the compound of the formula (1).
[II-4] The process according to [II-1], wherein the reaction of the compound of the formula (1) with hydroxylamine is performed in the presence of 100 mol % to 1000 mol % of water based on 1 mol of the compound of the formula (1).
[II-5] The process according to any one of [II-1] to [II-4], wherein the catalyst is an acid catalyst.
[II-6] The process according to [II-5], wherein the acid catalyst is one or more (preferably one to three, more preferably one or two, even more preferably one) acid(s) selected from the group consisting of mineral acids, carboxylic acids, and sulfonic acids.
[II-7] The process according to [II-5], wherein the acid catalyst is one or more (preferably one to three, more preferably one or two, even more preferably one) acid(s) selected from the group consisting of nitric acid, trifluoroacetic acid, maleic acid, and p-toluenesulfonic acid.
[II-8] The process according to [II-5], wherein the acid catalyst is trifluoroacetic acid.
[II-9] The process according to any one of [II-1] to [II-4], wherein the catalyst is an acid-base catalyst.
[II-10] The process according to [II-9], wherein the acid of the acid-base catalyst is one or more (preferably one to three, more preferably one or two, even more preferably one) acid(s) selected from the group consisting of mineral acids, carboxylic acids, and sulfonic acids.
[II-11] The process according to [II-9], wherein the acid of the acid-base catalyst is one or more (preferably one to three, more preferably one or two, even more preferably one) acid(s) selected from the group consisting of nitric acid, trifluoroacetic acid, maleic acid, and p-toluenesulfonic acid.
[II-12] The process according to [II-9], wherein the acid of the acid-base catalyst is trifluoroacetic acid.
[II-13] The process according to any one of [II-9] to [II-12], wherein the base of the acid-base catalyst is one or more (preferably one to three, more preferably one or two, even more preferably one) base(s) selected from the group consisting of N-methylaniline, morpholine, and pyrrolidine.
[II-14] The process according to any one of [II-9] to [II-12], wherein the base of the acid-base catalyst is N-methylaniline.
[II-15] The process according to any one of [II-1] to [II-14], wherein the hydroxylamine is a free hydroxylamine aqueous solution or a hydroxylamine salt.
[II-16] The process according to any one of [II-1] to [II-14], wherein the hydroxylamine is a 45% to 55% hydroxylamine aqueous solution, hydroxylamine hydrochloride, or hydroxylamine sulfate.
[II-17] The process according to any one of [II-1] to [II-14], wherein the hydroxylamine is a hydroxylamine salt, and the reaction is performed in the further presence of a neutralizing agent.
[II-18] The process according to any one of [II-1] to [II-14], wherein the hydroxylamine is hydroxylamine hydrochloride or hydroxylamine sulfate, and the reaction is performed in the further presence of a neutralizing agent.
[II-19] The process according to [II-17] or [II-18], wherein the neutralizing agent is sodium hydroxide, potassium hydroxide, sodium carbonate, potassium carbonate, sodium hydrogen carbonate, potassium hydrogen carbonate, or ammonia.
[II-20] The process according to any one of [II-1] to [II-19], wherein the reaction is performed in the presence of one or more (preferably one or two, more preferably one) solvent(s) selected from acetonitrile, toluene, xylene, chlorobenzene, dichlorobenzene, and dichloromethane, and a water solvent.
[II-21] The process according to any one of [II-1] to [II-19], wherein the reaction is performed in the presence of a solvent composed of a combination of water and dichlorobenzene (i.e., a mixed solvent of water and dichlorobenzene).
[II-22] The process according to any one of [II-1] to [II-21], wherein the compound of the formula (1) is prenal and the compound of the formula (3) is 5,5-dimethyl-4,5-dihydroisoxazole.

Advantageous Effects of Invention

The present invention provides a novel process for producing the compound of the formula (3). According to the present invention, a more industrially preferable process for producing the compound of the formula (3) is provided. Furthermore, according to the present invention, the compound of the formula (3) can be efficiently produced by a simple operation.

In the processes described in JP 2013-512202 A (Patent Document 2), Synlett 2008, No. 6, 827-830 (Non-Patent Document 1) and Chem. Eur. J. 2010, Vol. 16, 11325-11339 (Non-Patent Document 2), a ketone oxime that forms a ketone such as acetone or diethyl ketone as a by-product was used as a raw material. However, according to the present invention, it has been found that ketone oximes are unnecessary. Thus, the process of the present invention does not produce ketones as by-products and/or wastes. In other words, it has been found that a raw material having a minimum structure necessary for introducing the oximino moiety (—O—N=) of the target compound is hydroxylamine (HO—NH$_2$). As a result, the present inventor has succeeded in producing the target compound without using any ketone oximes. The process for producing the compound of the formula (3) using hydroxylamine of the present invention suppresses the generation of by-products and/or wastes and improves atom efficiency. Therefore, the production process of the present invention is industrially preferable, economical, and environmentally friendly.

In one embodiment of the present invention, the compound of the formula (3) is produced in the presence of water. In this embodiment, a highly safe, 50% hydroxylamine aqueous solution can be used instead of anhydrous hydroxylamine, which is highly explosive and dangerous.

According to the process described in JP 2013-512202 A (Patent Document 2), the compound of the formula (3) is produced under non-aqueous conditions. It is expected that the reaction intermediate of this process, an oxime, will hydrolyze back to an aldehyde and hydroxylamine in the presence of water. Furthermore, in the presence of water, the acid as a catalyst is diluted and inactivated, so that the reaction is expected to be difficult to proceed.

In fact, as shown in Reference Example 1 described later, the presence of water in the reaction system in the process of Patent Document 2 causes a significant decrease in yield. Therefore, those skilled in the art understand that the presence of water in the production of the compound of the formula (3) is not preferable.

In the process described in Patent Document 2 performed under non-aqueous conditions, if hydroxylamine is used instead of a ketone oxime, it is considered that there is no choice but to use anhydrous hydroxylamine, which is highly dangerous.

However, the present inventors have found that, as a result of performing a reaction with intentional use of hydroxylamine in the presence of water, the reaction proceeds surprisingly in a good yield. That is, the present inventors have found that, despite the suggestion of Patent Document 2, by using hydroxylamine in the presence of water, the compound of the formula (3) can be obtained safely and efficiently.

Therefore, according to the present invention, the target compound can be efficiently produced by a simple operation. Further, according to the present invention, the production of by-products and/or wastes can be suppressed, and atom efficiency can be improved. As a result, according to the present invention, there has been provided a process that can easily and inexpensively produce, on an industrial scale, an intermediate for producing a herbicide such as pyroxasulfone. Therefore, the process of the present invention is industrially preferable, economical, and environmentally friendly, and has high industrial utility value.

DESCRIPTION OF EMBODIMENTS

The present invention will be described in detail below.
The terms and symbols used herein will be explained below.
Examples of the halogen atom include fluorine atom, chlorine atom, bromine atom, and iodine atom.

(Ca-Cb) means that the number of carbon atoms is a to b. For example, "(C1-C4)" in "(C1-C4)alkyl" means that the number of the carbon atoms in the alkyl is 1 to 4.

Herein, it is to be understood that generic terms such as "alkyl" include both the straight chain and branched chain such as butyl and tert-butyl. However, when a specific term such as "butyl" is used, it is specific for "normal butyl", i.e., "n-butyl". In other words, the specific term "butyl" refers to "normal butyl", which is a straight chain. Branched chain isomers such as "tert-butyl" are referred to specifically when intended.

The prefixes "n-", "s-" and "sec-", "i-", "t-" and "tert-", "neo-", "c-" and "cyc-", "o-", "m-", and "p-" have their common meanings as follows: normal, secondary ("s-" and "sec-"), iso, tertiary ("t-" and "tert-"), neo, cyclo ("c-" and "cyc-"), ortho, meta, and para.

Herein, the following abbreviations may be used:
"Me" means methyl.
"Et" means ethyl.
"Pr", "n-Pr", and "Pr-n" mean propyl (i.e., normal propyl).
"i-Pr" and "Pr-i" mean isopropyl.
"Bu", "n-Bu", and "Bu-n" mean butyl (i.e., normal butyl).
"s-Bu" and "Bu-s" mean sec-butyl.
"i-Bu" and "Bu-i" mean isobutyl.
"t-Bu" and "Bu-t" mean tert-butyl.
"Pen", "n-Pen", and "Pen-n" mean pentyl (i.e., normal pentyl).
"Hex", "n-Hex", and "Hex-n" mean hexyl (i.e., normal hexyl).
"Dec", "n-Dec", and "Dec-n" mean decyl (i.e., normal decyl).
"c-Pr" and "Pr-c" mean cyclopropyl.
"c-Bu" and "Bu-c" mean cyclobutyl.
"c-Pen" and "Pen-c" mean cyclopentyl.
"c-Hex" and "Hex-c" mean cyclohexyl.
"Ph" means phenyl.
"Bn" means benzyl.
"Ms" means methylsulfonyl (CH$_3$SO$_2$—).
"Ts" means tosyl (4-CH$_3$—C$_6$H$_4$O$_2$—).
"Tf" means trifluoromethylsulfonyl (CF$_3$SO$_2$—).
"Ac" means acetyl (CH$_3$CO—).

The (C1-C6)alkyl means a straight or branched alkyl having 1 to 6 carbon atoms. Examples of the (C1-C6)alkyl include, but are not limited to, methyl, ethyl, propyl, isopropyl, butyl, sec-butyl, isobutyl, tert-butyl, pentyl, isopentyl, neopentyl, and hexyl.

The (C1-C4)alkyl means a straight or branched alkyl having 1 to 4 carbon atoms. Examples of the (C1-C4)alkyl are appropriate examples of the above-mentioned examples of the (C1-C6)alkyl.

The (C1-C6)haloalkyl means a straight or branched alkyl having 1 to 6 carbon atoms which is substituted with 1 to 13 same or different halogen atoms, wherein the halogen atoms have the same meaning as defined above. Examples of the (C1-C6)haloalkyl include, but are not limited to, fluoromethyl, difluoromethyl, trifluoromethyl, chlorodifluoromethyl, 2-fluoroethyl, 2-chloroethyl, 2,2,2-trifluoroethyl, pentafluoroethyl, 3-fluoropropyl, 3-chloropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 4-fluorobutyl, 4-chlorobutyl, 4-bromobutyl, 2,2,3,3,4,4,4-heptafluorobutyl, 5-fluoropenty, and 6-fluorohexyl.

The (C1-C4)haloalkyl means a straight or branched alkyl having 1 to 4 carbon atoms which is substituted with 1 to 9 same or different halogen atoms, wherein the halogen atoms have the same meaning as defined above. Examples of the (C1-C4)haloalkyl include, but are not limited to, appropriate examples of the above-mentioned examples of the (C1-C6) haloalkyl.

The (C3-C6)cycloalkyl means a cycloalkyl having 3 to 6 carbon atoms. Examples of the (C3-C6)cycloalkyl are cyclopropyl, cyclobutyl, cyclopentyl, and cyclohexyl.

The (C2-C6)alkenyl means a straight or branched alkenyl having 2 to 6 carbon atoms. Examples of the (C2-C6)alkenyl include, but are not limited to, vinyl, 1-propenyl, isopropenyl, 2-propenyl, 1-butenyl, 1-methyl-1-propenyl, 2-methyl-1-propenyl, 2-butenyl, 1,3-butadienyl, 1-pentenyl, and 1-hexenyl.

The (C2-C4)alkenyl means a straight or branched alkenyl having 2 to 4 carbon atoms. Examples of the (C2-C4) alkenyl include, but are not limited to, appropriate examples of the above-mentioned examples of the (C2-C6)alkenyl.

The (C2-C6)alkynyl means a straight or branched alkynyl having 2 to 6 carbon atoms. Examples of the (C2-C6)alkynyl include, but are not limited to, ethynyl, 1-propynyl, 2-propynyl, 1-butynyl, 1-methyl-2-propynyl, 2-butynyl, 1-pentynyl, and 1-hexynyl.

The (C2-C4)alkynyl means a straight or branched alkynyl having 2 to 4 carbon atoms. Examples of the (C2-C4)alkynyl include, but are not limited to, appropriate examples of the above-mentioned examples of the (C2-C6)alkynyl.

The (C1-C6)alkoxy means a (C1-C6)alkyl-O—, wherein the (C1-C6)alkyl moiety has the same meaning as defined above. Examples of the (C1-C6)alkoxy include, but are not limited to, methoxy, ethoxy, propoxy, isopropoxy, butoxy, sec-butoxy, isobutoxy, tert-butoxy, pentyloxy, isopentyloxy, neopentyloxy, and hexyloxy.

The (C1-C4)alkoxy means (C1-C4)alkyl-O—, wherein the (C1-C4)alkyl moiety has the same meaning as defined above. Examples of the (C1-C4)alkoxy include, but are not limited to, appropriate examples of the above-mentioned examples of the (C1-C6)alkoxy.

The cyclic hydrocarbon group means a cyclic group which is aromatic or non-aromatic and is monocyclic or multicyclic, wherein all of the ring-constituting atoms are carbon atoms.

In one embodiment, examples of the cyclic hydrocarbon group include, but are not limited to, a 3- to 14-membered (preferably 5- to 14-membered, more preferably 5- to 10-membered) cyclic hydrocarbon group which is aromatic or non-aromatic and is monocyclic, bicyclic, or tricyclic. In another embodiment, examples of the cyclic hydrocarbon group include, but are not limited to, a 4- to 8-membered (preferably 5- to 6-membered) cyclic hydrocarbon group which is aromatic or non-aromatic and is monocyclic or bicyclic (preferably monocyclic).

Examples of the cyclic hydrocarbon group include, but are not limited to, cycloalkyls and aryls.

The aryls are aromatic cyclic groups among the cyclic hydrocarbon groups as defined above.

The cyclic hydrocarbon group as defined or exemplified above may include a non-condensed cyclic group (e.g., a monocyclic group or a spirocyclic group) and a condensed cyclic group, when possible.

The cyclic hydrocarbon group as defined or exemplified above may be unsaturated, partially saturated, or saturated, when possible.

The cyclic hydrocarbon group as defined or exemplified above is also referred to as a carbocyclic ring group.

The carbocyclic ring is a ring which corresponds to the cyclic hydrocarbon group as defined or exemplified above.

Herein, there are no particular limitations on the "substituent(s)" for the phrase "optionally substituted" as long as they are chemically acceptable and exhibit the effects of the present invention.

Herein, examples of the "substituent(s)" for the phrase "optionally substituted" include, but are not limited to, one or more substituents (preferably 1 to 4 substituents) selected independently from Substituent Group (a).

Substituent Group (a) is a group comprising a halogen atom; a nitro group; a cyano group; a hydroxy group; an amino group; (C1-C6)alkyl; (C1-C6)haloalkyl; (C3-C6)cycloalkyl; (C2-C6)alkenyl; (C2-C6)alkynyl; (C1-C6)alkoxy; phenyl; and phenoxy.

In addition, one or more substituents (preferably 1 to 4 substituents) selected independently from Substituent Group (a) may each independently have one or more substituents (preferably 1 to 4 substituents) selected independently from Substituent Group (b).

In this context, Substituent Group (b) is the same as Substituent Group (a).

Herein, a compound having isomers includes all of the isomers and any mixture thereof in any ratio. For example, xylene includes o-xylene, m-xylene, p-xylene, and any mixture thereof in any ratio. For example, dichlorobenzene includes o-dichlorobenzene, m-dichlorobenzene, p-dichlorobenzene, and any mixture thereof in any ratio.

For example, when a compound has geometric isomers (cis-trans isomers), the (E)-isomer (anti-isomer), the (Z)-isomer (syn-isomer), and a mixture thereof are included within the scope of the present invention.

The process of the present invention includes the following scheme, wherein $R^1$ and $R^2$ are as described in [1] above.

[Chemical Formula 4]

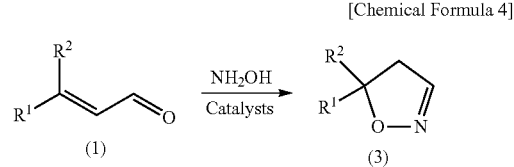

The process according to the present invention comprises a step of reacting a compound of the formula (1) (β-disubstituted-α,β-unsaturated aldehyde) with hydroxylamine (NH$_2$OH) in the presence of a catalyst to produce a compound of the formula (3) (5,5-disubstituted-4,5-dihydroisoxazole).

In the process of the present invention, the compound of the formula (1) is used. The compound of the formula (1) may be a known compound or can be produced from a known compound according to a known process.

(Raw Material; Compound of Formula (1))

Specific examples of the compound of the formula (1) include the following, but are not limited to, 3-methyl-2-buten-1-al (3-methyl-2-buten-1-al is also referred to as 3-methyl-2-butenal, 3-methylbut-2-enal, or prenal), 3-methyl-2-penten-1-al, 3-ethyl-2-penten-1-al, 3,4-dimethyl-2-penten-1-al, 3,4,4-trimethyl-2-penten-1-al, 4-chloro-3-methyl-2-buten-1-al, 4,4,4-trifluoro-3-methyl-2-buten-1-al, 3-cyclopropyl-2-buten-1-al, 2-cyclobutylideneacetaldehyde, 2-cyclopentylideneacetaldehyde, 2-cyclohexylideneacetaldehyde, 3-methyl-2-hepten-1-al, 3,7-dimethyl-2,6-octadien-1-al, 3,7-dimethyl-2-octan-1-al, 2-(9H-fluoren-9-ylidene)acetaldehyde, 3,3-diphenyl-2-propen-1-al, 3,3-bis(4-phenyl)-2-propen-1-al, 3,3-bis(4- methoxyphenyl)-2-propen-1-al, 3,3-bis(4-methoxyphenyl)-2-propen-1-al, 3-phenyl-2-buten-1-al, 3-(4-methylphenyl)-2-buten-1-al, 3-(4-methoxyphenyl)-2-buten-1-al, and 3-(4-chlorophenyl)-2-buten-1-al. From the viewpoints of the usefulness of the product, etc., preferable specific examples of the compound of the formula (1) is 3-methyl-2-buten-1-al.

(Product; Compound of Formula (3))

The product of the present invention is a 5,5-disubstituted-4,5-dihydroisoxazole corresponding to the compound of the formula (1) used as a raw material. Specific examples of the compound of the formula (3) include, but are not limited to, 5,5-dimethyl-4,5-dihydroisoxazole, 5-ethyl-5-methyl-4,5-dihydroisoxazole, 5,5-diethyl-4,5-dihydroisoxazole, 5-isopropyl-5-methyl-4,5-dihydroisoxazole, 5-(tert-butyl)-5-methyl-4,5-dihydroisoxazole, 5-(chloromethyl)-5-methyl-4,5-dihydroisoxazole, 5-methyl-5-(trifluoromethyl)-4,5-dihydroisoxazole, 5-cyclopropyl-5-methyl-4,5-dihydroisoxazole, 5-oxa-6-azaspiro[3.4]oct-6-ene, 1-methyl-2-methyl[4.4]non-2-ene, 1-methyl-2-methyl[4.5]dec-2-ene, 5-butyl-5-methyl-4,5-dihydroisoxazole, 5-methyl-5-(4-methylpent-3-en-1-yl)-4,5-dihydroisoxazole, 5-methyl-5-(4-methylpentyl)-4,5-dihydroisoxazole, 4'H-spiro[fluorene-9,5'-isoxazole], 5,5-diphenyl-4,5-dihydroisoxazole, 5,5-bis(4-methylphenyl)-4,5-dihydroisoxazole, 5,5-bis(4-methoxyphenyl)-4,5-dihydroisoxazole, 5,5-bis(4-chlorophenyl)-4,5-dihydroisoxazole, 5-methyl-5-phenyl-4,5-dihydroisoxazole, 5-ethyl-5-phenyl-4,5-dihydroisoxazole, 5-(4-methylphenyl)-5-methyl-4,5-dihydroisoxazole, 5-(4-methoxyphenyl)-5-methyl-4,5-dihydroisoxazole, and 5-(4-chlorophenyl)-5-methyl-4,5-dihydroisoxazole. From the viewpoints of the usefulness of the product, etc., preferable specific examples of the compound of the formula (3) is 5,5-dimethyl-4,5-dihydroisoxazole.

(Hydroxylamine)

The hydroxylamine to be used in the present invention is not particularly limited as long as the reaction proceeds and the safety is secured. Examples of the hydroxylamine include, but are not limited to, hydroxylamine (free) and salts thereof. Examples of the hydroxylamine (free) include, but are not limited to, a 50% hydroxylamine aqueous solution, a 60% hydroxylamine aqueous solution, a 70% hydroxylamine aqueous solution, an 80% hydroxylamine aqueous solution, and a 90% hydroxylamine aqueous solution. Generally, the "50% hydroxylamine aqueous solution" is also referred to as "hydroxylamine (50% solution in water)". Examples of the hydroxylamine salt include, but are not limited to, hydroxylamine hydrochloride, hydroxylamine sulfate, hydroxylamine nitrate (e.g., 50% solution in water), hydroxylamine carbonate, hydroxylamine phosphate, hydroxylamine acetate, and hydroxylamine oxalate.

The hydroxylamine to be used in the present invention (e.g., hydroxylamine (free) and salts thereof) may be used either alone or in a combination of two or more kinds in any ratio. The form of the hydroxylamine to be used in the present invention may be any form as long as the reaction proceeds and safety is ensured. Examples of the form include solid and liquid, and aqueous solutions and solutions in solvents other than water (e.g., organic solvents) with any concentration as long as the reaction proceeds and safety is ensured.

For example, when hydroxylamine (free) is used, the form of the hydroxylamine may be any form as long as the reaction proceeds and the safety is secured. In view of safety and economic efficiency, preferable examples of the form of the hydroxylamine (free) include an aqueous solution with a concentration of 10% or more and less than 70%, preferably an aqueous solution with a concentration of 45% or more and 55% or less.

In addition, from the viewpoints of safety, ease of handling, economic efficiency, etc., preferable examples of the hydroxylamine include a free hydroxylamine aqueous solution and hydroxylamine salts, more preferably a free hydroxylamine aqueous solution, hydroxylamine hydrochloride, and hydroxylamine sulfate, even more preferably a 45% to 55% hydroxylamine aqueous solution, hydroxylamine hydrochloride, and hydroxylamine sulfate, and still even more preferably a 45% to 50% hydroxylamine aqueous solution, hydroxylamine hydrochloride, and hydroxylamine sulfate.

From the viewpoints of yield, suppression of by-products, economic efficiency, etc., the amount of the hydroxylamine (e.g., hydroxylamine (free) and salts thereof) to be used in the present invention is as follows.

In one embodiment, it is in the range of 0.9 to 2.0 mol, preferably 0.9 to 1.5 mol, more preferably 0.9 to 1.2 mol, and even more preferably 0.9 to 1.1 mol, in terms of hydroxylamine ($NH_2OH$), based on 1 mol of the compound of the formula (1).

In another embodiment, it is in the range of 1.0 to 2.0 mol, preferably 1.0 to 1.5 mol, more preferably 1.0 to 1.2 mol, and even more preferably 1.0 to 1.1 mol, in terms of hydroxylamine ($NH_2OH$), based on 1 mol of the compound of the formula (1).

In yet another embodiment, it is in the range of 0.90 mol or more and less than 1.00 mol, preferably 0.90 mol or more and 0.99 mol or less, more preferably 0.90 mol or more and 0.98 mol or less, and even more preferably 0.93 mol or more and 0.97 mol or less, in terms of hydroxylamine ($NH_2OH$), based on 1 mol of the compound of the formula (1).

When using a hydroxylamine salt (e.g., hydroxylamine hydrochloride, hydroxylamine sulfate, etc.), the reaction of the present invention is preferably performed using a neutralizing agent. The neutralizing agent is a base for neutralizing the hydroxylamine salt to release free hydroxylamine. Examples of the neutralizing agent include, but are not limited to, alkali metal hydroxides (e.g., lithium hydroxide, sodium hydroxide, and potassium hydroxide), alkaline earth metal hydroxides (e.g., magnesium hydroxide, calcium hydroxide, and barium hydroxide), alkali metal carbonates (e.g., lithium carbonate, sodium carbonate, and potassium carbonate), alkaline earth metal carbonates (e.g., magnesium carbonate, calcium carbonate, and barium carbonate), alkali metal hydrogen carbonates (e.g., lithium hydrogen carbonate, sodium hydrogen carbonate, and potassium hydrogen carbonate), alkali metal carboxylates (e.g., lithium acetate, sodium acetate, and potassium acetate), amines (e.g., triethylamine, tributylamine, diisopropylethylamine, 1,8-diazabicyclo[5.4.0]-7-undec-7-ene (DBU), and pyridine), ammonia (e.g., 25 to 30% aqueous ammonia and ammonia gas, preferably 25 to 30% aqueous ammonia). Preferable examples of the neutralizing agent include sodium hydroxide, potassium hydroxide, sodium carbonate, potassium carbonate, sodium hydrogen carbonate, potassium hydrogen carbonate, and ammonia, more preferably include sodium hydroxide, sodium carbonate, sodium hydrogen carbonate, and ammonia, and even more preferably sodium hydroxide. Examples of the sodium hydroxide include, but are not limited to, sodium hydroxide beads, a 48% sodium hydroxide aqueous solution, a 25% sodium hydroxide aqueous solution, and a 10% sodium hydroxide aqueous solution, preferably a 48% sodium hydroxide aqueous solution and a 25% sodium hydroxide aqueous solution, and more preferably a 48% sodium hydroxide aqueous solution. The neutralizing agent may be used either alone or in a combination of two or more kinds thereof in any ratio. The neutralizing agent may be in any form as long as the reaction proceeds. Examples of the form include a solid of only the neutralizing agent, a liquid of only the neutralizing agent, and a gas of only the neutralizing agent, an aqueous solution with any concentration, and solutions in a solvent other than water (e.g., an organic solvent) with any concentration. The form of the neutralizing agent can be appropriately selected by a person skilled in the art.

The amount of the neutralizing agent to be used may be any amount as long as the reaction proceeds. Examples of the amount of the neutralizing agent to be used include an amount in which the hydroxylamine salt can be neutralized to release free hydroxylamine. From the viewpoints of yield, suppression of by-products, economic efficiency, etc., 0.9 to 1.1 equivalents, and preferably 0.9 to 1.0 equivalent based on 1 equivalent of the hydroxylamine salt can be mentioned as examples. However, the amount can be adjusted appropriately by a person skilled in the art.

(Solvent)

From the viewpoints of smooth progress of the reaction, safety, etc., it is preferable to perform the reaction of the present invention in the presence of a solvent. The solvent may be any solvent as long as the reaction of the present invention proceeds and safety is ensured. Examples of the solvent include, but are not limited to, water, alcohols (e.g., methanol, ethanol, 2-propanol, butanol, and tert-butanol (tert-butanol is also referred to as tert-butyl alcohol)), ethers (e.g., tetrahydrofuran (THF), 1,4-dioxane, diisopropyl ether, dibutyl ether, di-tert-butyl ether, cyclopentyl methyl ether (CPME), methyl tert-butyl ether, 1,2-dimethoxyethane (DME), diglyme, and triglyme), nitriles (e.g., acetonitrile), amides (e.g., N,N-dimethylformamide (DMF), N,N-dimethylacetamide (DMAC), and N-methylpyrrolidone (NMP)), alkyl ureas (e.g., N,N'-dimethylimidazolidinone (DMI)), sulfoxides (e.g., dimethyl sulfoxide (DMSO)), sulfones (e.g., sulfolane), carboxylic acid esters (e.g., ethyl acetate and butyl acetate), aromatic hydrocarbon derivatives (e.g., benzene, toluene, xylenes, chlorobenzene, dichlorobenzenes, and nitrobenzene), halogenated aliphatic hydrocarbons (e.g., dichloromethane, chloroform, and 1,2-dichloroethane (EDC)), aliphatic hydrocarbons (e.g., hexane, heptane, octane, cyclohexane, and ethylcyclohexane), and any combination thereof in any ratio. However, from the viewpoint of safety in using hydroxylamine, the reaction of the present invention is preferably performed in the presence of water. In any case, the solvent may be in a single layer or may be separated into two layers as long as the reaction proceeds.

From the viewpoints of reactivity, yield, safety, economic efficiency, etc., in one embodiment, preferable examples of the solvent include water, alcohols, nitriles, ethers, aromatic hydrocarbon derivatives, halogenated aliphatic hydrocarbons, and any combination thereof in any ratio, more preferably water, nitriles, aromatic hydrocarbon derivatives, halogenated aliphatic hydrocarbons, and any combination thereof in any ratio, even more preferably water, aromatic hydrocarbon derivatives, halogenated aliphatic hydrocarbons, and any combination thereof in any ratio, and particularly preferably a combination of water and a halogenated aliphatic hydrocarbon in any ratio. Preferable specific examples of the solvent include water, methanol, ethanol, 2-propanol, tert-butanol, acetonitrile, tetrahydrofuran (THF), toluene, xylene, chlorobenzene, dichlorobenzene, dichloromethane, and any combination thereof in any ratio, more preferably water, acetonitrile, toluene, xylene, chlorobenzene, dichlorobenzene, dichloromethane, and any combination thereof in any ratio, even more preferably water, toluene, xylene, chlorobenzene, dichlorobenzene, dichloromethane, and any combination thereof in any ratio, and particularly preferably a combination of water and dichloromethane in any ratio. In any case, the presence of water is preferred. In either case, the solvent may be in a single layer or may be separated into two layers as long as the reaction proceeds.

From the same viewpoints as described above, in another embodiment, preferable examples of the solvent include water, alcohols, nitriles, ethers, aromatic hydrocarbon derivatives, halogenated aliphatic hydrocarbons, and any combination thereof in any ratio, more preferably water, alcohols, nitriles, halogenated aliphatic hydrocarbons, and any combination thereof in any ratio, even more preferably water, nitriles, halogenated aliphatic hydrocarbons, and any combination thereof in any ratio, and particularly preferably a combination of water and a halogenated aliphatic hydrocarbon in any ratio. Preferable specific examples of the solvent include water, methanol, ethanol, 2-propanol, tert-butanol, acetonitrile, tetrahydrofuran (THF), toluene, xylene, chlorobenzene, dichlorobenzene, dichloromethane, and any combination thereof in any ratio, more preferably water, methanol, ethanol, 2-propanol, tert-butanol, acetonitrile, dichloromethane, and any combination thereof in any ratio, even more preferably water, acetonitrile, dichloromethane, and any combination thereof in any ratio, and particularly preferably a combination of water and dichloromethane in any ratio. In any case, the presence of water is preferred. In either case, the solvent may be in a single layer or may be separated into two layers as long as the reaction proceeds.

The water derived from the hydroxylamine aqueous solution can be understood as a solvent. When a neutralizing agent is used with a hydroxylamine salt (e.g., hydroxylamine hydrochloride, hydroxylamine sulfate, etc.), the water derived from the aqueous solution of the neutralizing agent (e.g., a 48% sodium hydroxide aqueous solution) can also be understood as a solvent. The water produced by the neutralization can also be understood as a solvent.

The amount of the solvent used may be any amount as long as the reaction system can be sufficiently stirred. From the viewpoints of yield, suppression of by-products, economic efficiency, etc., it is, for example, in the range of more than 0 (zero) and 10 L (liters) or less, preferably 0.001 to 5 L, 0.001 to 0.5 L, 0.001 to 0.2 L, preferably 0.01 to 5 L, 0.01 to 0.5 L, 0.01 to 0.2 L, more preferably 0.02 to 0.5 L, and further preferably 0.02 to 0.2 L based on 1 mol of the compound of the formula (1). When a combination of two or more solvents is used, the ratio of the two or more solvents may be any ratio as long as the reaction proceeds.

Further, from the viewpoint of safety in using hydroxylamine, the reaction of the present invention is preferably performed in the presence of water. From the viewpoints of safety, economic efficiency, etc., the amount of the water is as follows.

In one embodiment, the amount of the water is, for example, 50 mol % or more, preferably 100 mol % or more, more preferably 150 mol % or more, and even more preferably 180 mol % or more, based on 1 mol of the compound of the formula (1).

In another embodiment, it is 50 mol % to 6000 mol %, preferably 50 mol % to 3000 mol %, more preferably 50 mol % to 1500 mol %, further preferably 50 mol % to 1000 mol %, further preferably 50 mol % to 800 mol %, further preferably 50 mol % to 500 mol %, further preferably 50 mol % to 400 mol %, and further preferably 50 mol % to 350 mol %.

In yet another embodiment, it is 100 mol % to 6000 mol %, preferably 100 mol % to 3000 mol %, more preferably 100 mol % to 1500 mol %, further preferably 100 mol % to 1000 mol %, further preferably 100 mol % to 800 mol %, further preferably 100 mol % to 500 mol %, further preferably 100 mol % to 400 mol %, and further preferably 100 mol % to 350 mol %.

In yet another embodiment, it is 150 mol % to 6000 mol %, preferably 150 mol % to 3000 mol %, more preferably 150 mol % to 1500 mol %, further preferably 150 mol % to 1000 mol %, further preferably 150 mol % to 800 mol %, further preferably 150 mol % to 500 mol %, further preferably 150 mol % to 400 mol %, and further preferably 150 mol % to 350 mol %.

In yet another embodiment, it is 180 mol % to 6000 mol %, preferably 180 mol % to 3000 mol %, more preferably 180 mol % to 1500 mol %, further preferably 180 mol % to 1000 mol %, further preferably 180 mol % to 800 mol %, further preferably 180 mol % to 500 mol %, further preferably 180 mol % to 400 mol %, and further preferably 180 mol % to 350 mol %.

(Reaction Temperature)

The reaction temperature is not particularly limited. From the viewpoints of yield, suppression of by-products, economic efficiency, etc., the reaction temperature may be, for example, in the range of −30° C. (minus 30° C.) to 160° C., preferably 0° C. to 80° C., more preferably 20° C. to 80° C., even more preferably 20° C. to 60° C., and further preferably 30° C. to 50° C.

In embodiments where an acid catalyst is used as the catalyst, the reaction proceeds satisfactorily in industrially preferable temperature ranges (for example, 40 to 60° C.) as understood from Examples.

The embodiment that involves using an acid-base catalyst as the catalyst has a further advantage that the reaction proceeds satisfactorily even at a relatively low temperature (for example, 20 to 40° C.), as will be understood from Examples.

However, the reaction temperature of the present invention is not limited to these temperature ranges.

(Reaction Time)

The reaction time is not particularly limited. From the viewpoints of yield, suppression of by-products, economic efficiency, etc., the reaction time may be, for example, in the range of 0.5 hours to 96 hours, preferably 1 hour to 50 hours, more preferably 6 hours to 50 hours, and even more preferably 6 hours to 24 hours.

(Catalyst)

From the viewpoint of smooth progress of a reaction, the reaction of the present invention is performed in the presence of a catalyst. The catalyst to be used in the present invention is preferably an acid catalyst or an acid-base catalyst.

(Acid Catalyst)

In one embodiment of the present invention, the compound of the formula (3) is produced in the presence of an acid catalyst. The acid catalyst may be any acid catalyst as long as the reaction proceeds. In addition, as long as the reaction proceeds, any of the following forms may be used and are included within the scope of the present invention. A free acid can be used as the acid catalyst. The acid catalyst may be used in the form of a partial salt. When the acid catalyst is a partial salt, the acid catalyst may be either a simple salt or a double salt. The acid catalyst may be used in the form of an anhydride. The acid catalyst may be used in the form of a hydrate. The acid catalyst may be used in the form of a dimer, a trimer, or a higher multimer.

Examples of the acid catalyst include, but are not limited to, the following.

a) Mineral Acids

As the acid catalyst, a mineral acid may be used. Specific examples of the mineral acid include, but are not limited to, hydrochloric acid, sulfuric acid, and nitric acid.

b) Carboxylic Acids

As the acid catalyst, a carboxylic acid may be used. As long as the reaction proceeds, the carboxylic acid may be used in the form of a free acid or may be used in the form of an anhydride thereof.

In one embodiment, examples of the carboxylic acid include saturated or unsaturated aliphatic (C1-C8)monocarboxylic, dicarboxylic, and tricarboxylic acids optionally substituted by one or more halogen atoms, and aromatic (C7-C11)monocarboxylic, dicarboxylic, and tricarboxylic acids optionally substituted by one or more substituents independently selected from halogen atoms, (C1-C4)alkyl, and (C1-C4)haloalkyl. In polycarboxylic acids such as dicarboxylic acids and tricarboxylic acids, a plurality of carboxy groups may be partially in the form of salt as long as the reaction proceeds. Examples of preferable carboxylic acids include saturated or unsaturated aliphatic (C1-C8) carboxylic acids optionally substituted by one or more halogen atoms. Examples of the carboxylic acid anhydride include their anhydrides. In another embodiment, examples of the carboxylic acid include saturated or unsaturated aliphatic (C1-C8)carboxylic acids optionally substituted by one or more halogen atoms, and benzoic acid optionally substituted by one or more substituents independently selected from halogen atoms, (C1-C4)alkyl, and (C1-C4) haloalkyl. Examples of preferable carboxylic acids include saturated or unsaturated aliphatic (C1-C8)carboxylic acids optionally substituted by one or more halogen atoms. Examples of the carboxylic acid anhydride include their anhydrides.

Specific examples of the carboxylic acid include acetic acid, trifluoroacetic acid, trichloroacetic acid, dichloroacetic acid, maleic acid, citric acid, benzoic acid, and phthalic acid. Specific examples of the carboxylic anhydride include trifluoroacetic anhydride, maleic anhydride, and phthalic anhydride. Thus, for example, maleic acid may be maleic anhydride.

c) Sulfonic Acids

A sulfonic acid can be used as the acid catalyst. As long as the reaction proceeds, the sulfonic acid may be used as a free acid or an anhydride thereof. Specific examples of the sulfonic acid include methanesulfonic acid, trifluoromethanesulfonic acid (TfOH), benzenesulfonic acid, p-toluenesulfonic acid (TsOH), and 10-camphorsulfonic acid (CSA). In the present description, "p-toluenesulfonic acid (TsOH)" includes "p-toluenesulfonic acid monohydrate (TsOH·H$_2$O)". Specific examples of the sulfonic anhydride include methanesulfonic anhydride and trifluoromethanesulfonic anhydride.

d) Phosphoric Acids and Derivatives Thereof

Phosphoric acids and derivatives thereof can be used as the acid catalyst. The phosphoric acids and derivatives thereof are not particularly limited as long as they are chemically acceptable and exhibit the effects of the present invention. Examples of the phosphoric acids and derivatives thereof include, but are not limited to, the following.

d-1) Phosphoric Acids

As long as the reaction proceeds, the phosphoric acid may be used in the form of a free acid, or one or more OH groups in the molecule thereof may partially form a salt. In addition, phosphoric acid may be its anhydride or the like. Examples of phosphoric acids include phosphoric acid (orthophosphoric acid; $H_3PO$), ammonium dihydrogen phosphate, polyphosphoric acid, pyrophosphoric acid (diphosphoric acid), and diphosphorus pentoxide.

d-2) Phosphoric Acid Monoesters

As long as the reaction proceeds, the phosphoric acid monoester may be used in the form of a free acid, or one or more OH groups in the molecule thereof may partially form a salt. The phosphoric acid monoester may be used in the form of its anhydride as long as it is chemically acceptable. Specific examples of the phosphoric acid monoester include ethyl phosphate (i.e., ethyl dihydrogen phosphate; $(C_2H_5O)P(=O)(OH)_2$) and phenyl phosphate (i.e., phenyl dihydrogen phosphate; $(C_6H_5O)P(=O)(OH)_2$).

d-3) Phosphoric Acid Diesters

As long as the reaction proceeds, the phosphoric acid diester may be used in the form of a free acid, or as it may be used in the form of an anhydride thereof as long as it is chemically acceptable. Specific examples of phosphoric acid diesters include diethyl phosphate (i.e., diethyl hydrogen phosphate; $(C_2H_5O)_2P(=O)OH$) and diphenyl phosphate (i.e., diphenyl hydrogen phosphate; $(C_6H_5O)_2P(=O)OH$).

e) Solid Acids

As the acid catalyst, a solid acid may be used.

Examples of the solid acid include, but are not limited to, cation exchange resins, heteropoly acids, zeolites, montmorillonite, and alumina.

Herein, the term "cation exchange resin" is not particularly limited and means a known strongly acidic or weakly acidic cation exchange resin. Specific examples of the cation exchange resin include, but are not limited to, the DIAION (registered trademark) Series (e.g., DIAION SK1B, SK110, SK116, P206, and WK40) manufactured by Mitsubishi Chemical Corporation, the AMBERLITE (registered trademark) Series (e.g., AMBERLITE IR-120B, IR-200CT, IRC50, and IR-124) manufactured by Rohm and Haas Company, and the DOWEX (registered trademark) series (e.g., 50W-X8) manufactured by The Dow Chemical Company.

Examples of the heteropoly acids include, but are not limited to, 12-molybdo(VI)phosphoric acid n-hydrate ($H_3[PMo_{12}O_{40}] \cdot nH_2O$ (n≈30)), 12-tungsto(VI)phosphoric acid n-hydrate ($H_3[PW_{12}O_{40}] \cdot nH_2O$ (n≈30)), and 12-tungsto(VI) silicic acid n-hydrate ($H_4[SiW_{12}O_{40}] \cdot nH_2O$ (e.g., n≈26)). 12-Molybdo(VI)phosphoric acid n-hydrate is also referred to as phosphomolybdic acid n-hydrate. 12-Tungsto(VI) phosphoric acid n-hydrate is also referred to as phosphotungstic acid n-hydrate. 12-Tungsto(VI)silicic acid n-hydrate is also referred to as silicotungstic acid n-hydrate.

As the acid catalyst, a salt of heteropoly acid may also be used. Specific examples of the salt of heteropoly acid include, but are not limited to, sodium 12-molybdo(VI) phosphate n-hydrate($Na_3[PMo_{12}O_{40}] \cdot nH_2O$ (n≈30)). Sodium 12-molybdo(VI)phosphate n-hydrate is also referred to as sodium phosphomolybdate n-hydrate.

Examples of the zeolite include, but are not limited to, ZSM-5 type, mordenite type, L type, Y type, X type, and beta type.

From the viewpoints of yield, economic efficiency, etc., preferable examples of the acid catalyst are as follows, but are not limited thereto.

One or more (preferably one to three, more preferably one or two, and even more preferably one) acid(s) selected from the group consisting of mineral acids, carboxylic acids, sulfonic acids, and phosphoric acids are preferable.

One or more (preferably one to three, more preferably one or two, and even more preferably one) acid(s) selected from the group consisting of mineral acids, carboxylic acids, and sulfonic acids are more preferable.

From the same viewpoints as described above, specific preferable examples of the acid catalyst are as follows, but are not limited thereto.

One or more (preferably one to three, more preferably one or two, and even more preferably one) acid(s) selected from the group consisting of hydrochloric acid, sulfuric acid, nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, phosphoric acid, ethyl phosphate, phenyl phosphate, diethyl phosphate, and diphenyl phosphate are preferable.

One or more (preferably one to three, more preferably one or two, and even more preferably one) acid(s) selected from the group consisting of nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, and diphenyl phosphate are more preferable.

One or more (preferably one to three, more preferably one or two, and even more preferably one) acid(s) selected from the group consisting of nitric acid, trifluoroacetic acid, trichloroacetic acid, dichloroacetic acid, maleic acid, maleic anhydride, methanesulfonic acid, trifluoromethanesulfonic acid, benzenesulfonic acid, and p-toluenesulfonic acid are further preferable.

One or more (preferably one to three, more preferably one or two, and even more preferably one) acid(s) selected from the group consisting of nitric acid, trifluoroacetic acid, trichloroacetic acid, maleic acid, maleic anhydride, benzenesulfonic acid, and p-toluenesulfonic acid are further preferable.

One or more (preferably one to three, more preferably one or two, and even more preferably one) acid(s) selected from the group consisting of nitric acid, trifluoroacetic acid, trichloroacetic acid, maleic acid, maleic anhydride, and p-toluenesulfonic acid are further preferable.

One or more (preferably one to three, more preferably one or two, and even more preferably one) acid(s) selected from the group consisting of nitric acid, trifluoroacetic acid, maleic acid, maleic anhydride, and p-toluenesulfonic acid are further preferable.

One or more (preferably one to three, more preferably one or two, and even more preferably one) acid(s) selected from the group consisting of nitric acid, trifluoroacetic acid, maleic acid, and p-toluenesulfonic acid are further preferable.

One or more (preferably one to three, more preferably one or two, and even more preferably one) acid(s) selected from the group consisting of nitric acid, trifluoroacetic acid, maleic acid, and maleic anhydride are also further preferable.

One to three (preferably one or two, and more preferably one) acid(s) selected from the group consisting of trifluoroacetic acid, maleic acid, and maleic anhydride are further preferable.

One or two (preferably one) acid(s) selected from the group consisting of trifluoroacetic acid and maleic acid are further preferable.

Trifluoroacetic acid is more preferable.

The acid catalyst may be used either alone or in a combination of two or more kinds thereof in any ratio. The acid catalyst may be in any form as long as the reaction proceeds. Examples of the form include a solid, liquid, or gas of only the acid catalyst, and an aqueous solution with any concentration or a solution in a solvent other than water (e.g., an organic solvent) with any concentration. The form can be appropriately selected by those skilled in the art.

The amount of the acid catalyst to be used may be any amount as long as the reaction proceeds. From the viewpoints of yield, suppression of by-products, economic efficiency, etc., it may be, for example, in the range of 0.01 to 1.0 mol, preferably 0.01 to 0.30 mol, more preferably 0.02 to 0.30 mol, 0.02 to 0.20 mol, and 0.02 to 0.10 mol based on 1 mol of the compound of the formula (1).

In embodiments where an acid catalyst is used as the catalyst, the amount of hydroxylamine to be used may be in the range of 0.5 to 2 mol, preferably 0.9 to 1.5 mol, more preferably 0.9 to 1.2 mol and 1.0 to 1.2 mol, and even more preferably 0.9 to 1.1 mol and 1.0 to 1.1 mol, based on 1 mol of the compound of the formula (1).

(Acid-Base Catalyst)

In another embodiment of the present invention, the compounds of the formula (3) are produced in the presence of an acid-base catalyst. Acid-base catalysts are mixtures of acids and bases. The acid-base catalyst may be any acid-base catalyst as long as the reaction proceeds. In addition, as long as the reaction proceeds, any form may be used and is included within the scope of the present invention.

When the acid-base catalyst is a salt, the acid-base catalyst may be either a simple salt or a double salt. The acid-base catalyst may be used in the form of an anhydride. The acid-base catalyst may be used in the form of a hydrate. The acid and/or the base of the acid-base catalyst may be used in the form of a dimer or the like.

The acid-base catalyst may be used either alone or in a combination of two or more kinds thereof in any ratio. The acid-base catalyst may be in any form as long as the reaction proceeds. Examples of the form include a solid or liquid of only the acid-base catalyst, and an aqueous solution or a solution in a solvent other than water (e.g., an organic solvent) with any concentration. The form can be appropriately selected by those skilled in the art.

As the acid of the acid-base catalyst, the acids mentioned as examples of the acid catalyst described above may be used.

From the viewpoints of yield, economic efficiency, etc., preferable examples of the acid of the acid-base catalyst are as follows, but are not limited thereto.

One or more (preferably one to three, more preferably one or two, and even more preferably one) acid(s) selected from the group consisting of mineral acids, carboxylic acids, sulfonic acids, and phosphoric acids are preferable.

One or more (preferably one to three, more preferably one or two, and even more preferably one) acid(s) selected from the group consisting of mineral acids, carboxylic acids, and sulfonic acids are preferable.

One or more (preferably one to three, more preferably one or two, and even more preferably one) acid(s) selected from the group consisting of mineral acids and carboxylic acids are more preferable.

From the same viewpoints as described above, specific preferable examples of the acid of the acid-base catalyst are as follows, but are not limited thereto.

One or more (preferably one to three, more preferably one or two, and even more preferably one) acid(s) selected from the group consisting of hydrochloric acid, sulfuric acid, nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, phosphoric acid, ethyl phosphate, phenyl phosphate, diethyl phosphate, and diphenyl phosphate are preferable.

One or more (preferably one to three, more preferably one or two, and even more preferably one) acid(s) selected from the group consisting of nitric acid, trifluoroacetic acid, trichloroacetic acid, dichloroacetic acid, maleic acid, maleic anhydride, methanesulfonic acid, trifluoromethanesulfonic acid, benzenesulfonic acid, p-toluenesulfonic acid, 10-camphorsulfonic acid, and diphenyl phosphate are more preferable.

One or more (preferably one to three, more preferably one or two, and even more preferably one) acid(s) selected from the group consisting of nitric acid, trifluoroacetic acid, trichloroacetic acid, dichloroacetic acid, maleic acid, maleic anhydride, methanesulfonic acid, trifluoromethanesulfonic acid, benzenesulfonic acid, and p-toluenesulfonic acid are further preferable.

One or more (preferably one to three, more preferably one or two, and even more preferably one) acid(s) selected from the group consisting of nitric acid, trifluoroacetic acid, trichloroacetic acid, maleic acid, maleic anhydride, benzenesulfonic acid, and p-toluenesulfonic acid are further preferable.

One or more (preferably one to three, more preferably one or two, and even more preferably one) acid(s) selected from the group consisting of nitric acid, trifluoroacetic acid, trichloroacetic acid, maleic acid, maleic anhydride, and p-toluenesulfonic acid are further preferable.

One or more (preferably one to three, more preferably one or two, and even more preferably one) acid(s) selected from the group consisting of nitric acid, trifluoroacetic acid, maleic acid, maleic anhydride, and p-toluenesulfonic acid are further preferable.

One or more (preferably one to three, more preferably one or two, and even more preferably one) acid(s) selected from the group consisting of nitric acid, trifluoroacetic acid, maleic acid, and p-toluenesulfonic acid are further preferable.

One or more (preferably one to three, more preferably one or two, and even more preferably one) acid(s) selected from the group consisting of nitric acid, trifluoroacetic acid, maleic acid, and maleic anhydride are also further preferable.

One to three (preferably one or two, and more preferably one) acid(s) selected from the group consisting of nitric acid, trifluoroacetic acid, and maleic acid are further preferable.

One to three (preferably one or two, and more preferably one) acid(s) selected from the group consisting of trifluoroacetic acid, maleic acid, and maleic anhydride are also further preferable.

One or two (preferably one) acid(s) selected from the group consisting of trifluoroacetic acid and maleic acid are further preferable.

Trifluoroacetic acid is more preferable.

As the base of the acid-base catalyst, an amine is preferable.

The amine may be a primary amine, secondary amine, tertiary amine, or heterocyclic amine having the following formula:

$R^3R^4R^5N$ wherein $R^3$, $R^4$, and $R^5$ are each independently hydrogen, an optionally substituted (C1-C6)alkyl; an optionally substituted (C3-C6)cycloalkyl, an optionally substituted (C2-C6)alkenyl; an optionally substituted (C2-C6)alkynyl; or an optionally substituted aryl; or any two of $R^3$, $R^4$, and $R^5$, together with the nitrogen atom to which they are attached form a 4- to 12-membered heterocyclic ring, wherein the formed ring is optionally substituted; provided that at least one of $R^3$, $R^4$, and $R^5$ is not hydrogen.

Specific examples of the primary amine include, but are not limited to, methylamine, ethylamine, propylamine, butylamine, and aniline.

Specific examples of the secondary amine include, but are not limited to, diethylamine, dipropylamine, diisopropylamine, N-methylaniline (PhNHMe), N-ethylaniline, piperidine, and morpholine.

Specific examples of the tertiary amine include, but are not limited to, triethylamine, tripropylamine, tributylamine, diisopropylethylamine, 1,4-diazabicyclo[2.2.2]octane (DABCO), N,N-dimethylaniline, and N,N-diethylaniline.

Specific examples of the heterocyclic amine include, but are not limited to, pyridine, 4-(dimethylamino)-pyridine, 4-pyrrolidinopyridine, 2,6-lutidine, quinoline, isoquinoline, 1,8-diazabicyclo[5.4.0]-7-undec-7-ene (DBU), and 1,5-diazabicyclo[4.3.0]non-5-ene (DBN).

4-(Dimethylamino)-pyridine, 4-pyrrolidinopyridine, 1,8-diazabicyclo[5.4.0]-7-undec-7-ene (DBU), and 1,5-diazabicyclo[4.3.0]non-5-ene (DBN) also belong to the tertiary amine.

Examples of the amine also include imidazolinones. Specific examples of the imidazolinones include optical isomers such as (2S,5S)-2-tert-butyl-3-methyl-5-benzyl-4-imidazolinone and its diastereomers, and analogs thereof. However, since imidazolinones are expensive, it is industrially preferable not to use imidazolinones.

From the viewpoints of yield, economic efficiency, etc., preferable examples of the base of the acid-base catalyst include secondary amines. Preferable specific examples of the base of the acid-base catalyst include N-methylaniline, morpholine, and pyrrolidine, and more preferably include N-methylaniline.

The amount of the acid-base catalyst to be used may be any amount as long as the reaction proceeds. The ratio of the acid to the base of the acid-base catalyst may be 1:1 or may not be 1:1.

From the viewpoints of yield, suppression of by-products, economic efficiency, etc., the amount of the acid of the acid-base catalyst to be used may be, for example, in the range of 0.001 to 1.00 mol, preferably 0.005 to 0.30 mol and 0.005 to 0.10 mol, more preferably 0.01 to 0.10 mol and 0.01 to 0.05 mol, based on 1 mol of the compound of the formula (1).

From the viewpoints of yield, suppression of by-products, economic efficiency, etc., the amount of the base of the acid-base catalyst to be used may be, for example, in the range of 0.001 to 1.00 mol, preferably 0.005 to 0.30 mol and 0.005 to 0.10 mol, more preferably 0.01 to 0.10 mol and 0.01 to 0.05 mol, based on 1 mol of the compound of the formula (1).

In embodiments where an acid-base catalyst is used as the catalyst, the amount of hydroxylamine to be used may be in the range of 0.5 to 2 mol, 0.9 to 1.5 mol, and 0.9 to 1.2 mol, based on 1 mol of the compound of the formula (1). From the viewpoints of yield, economic efficiency, etc., the amount of hydroxylamine to be used is preferably smaller than that of the compound of the formula (1) in embodiments where an acid-base catalyst is used as the catalyst. In one embodiment, the amount of hydroxylamine to be used may be, for example, less than 1.00 mol, preferably 0.99 mol or less, and more preferably 0.98 mol or less, based on 1 mol of the compound of the formula (1). In another embodiment, it may be, for example, in the range of 0.90 mol or more and 1.00 mol or less, preferably 0.90 mol or more and less than 1.00 mol, more preferably 0.90 mol or more and 0.99 mol or less, and even more preferably 0.90 mol or more and 0.98 mol or less, based on 1 mol of the compound of the formula (1).

Unless otherwise indicated, it is understood that numbers used herein to express characteristics such as quantities, sizes, concentrations, and reaction conditions are modified by the term "about". In some embodiments, disclosed numerical values are interpreted applying the reported number of significant digits and conventional rounding techniques. In some embodiments, disclosed numerical values are interpreted as containing certain errors necessarily resulting from the standard deviation found in their respective testing measurements.

Hereinafter, the present invention will be described in more detail by Examples, but the present invention is not limited in any way by these Examples.

Herein, the following instruments and conditions were used for the analysis in Examples and Comparative Examples.

($^1$H-NMR: 1H Nuclear Magnetic Resonance Spectrum)
Instrument: JEOL JMN-ECS-300 or JEOL JMN-Lambda-400 (manufactured by JEOL RESONANCE Ltd.), solvent: CDCl$_3$ and/or DMSO-d$_6$, internal standard substance: tetramethylsilane (TMS) and others.

($^{13}$C-NMR: $^{13}$C Nuclear Magnetic Resonance Spectrum)
$^{13}$C-NMR was measured using the same equipment, solvent, and reference substance as for H-NMR.

(GC Analysis: Gas Chromatography Analysis)
GC-2025 (manufactured by Shimadzu Corporation), detection method: FID Gas chromatography (GC) analysis method; regarding the GC analysis method, the following documents can be referred to, if necessary.

Document (a): "Shin-Jikkenkagaku Koza 9, Bunseki Kagaku II (A New Course in Experimental Chemistry 9, Analytical Chemistry II)", pp. 60 to 86 (1977), edited by The Chemical Society of Japan, published by Shingo Iizumi, Maruzen Co., Ltd. (for example, page 66 of this document can be referred to with respect to liquids for a stationary phase to be usable for a column).

Document (b): "Jikkenkagaku Koza 20-1, Bunseki Kagaku (A Course in Experimental Chemistry 20-1, Analytical Chemistry)", 5th edition, pp. 121 to 129 (2007), edited by The Chemical Society of Japan, published by Seishiro Murata, Maruzen Co., Ltd. (for example, pages 124 to 125 of this document can be referred to with respect to the specific usage of hollow capillary separation columns).

(GC-MS Analysis: gas chromatography mass spectrometry analysis)
Analysis instrument: 6890N Network GC System (manufactured by Agilent Technologies), mass detector: 5973N MSD (manufactured by Agilent Technologies)

Example 1

Production of 5,5-dimethyl-4,5-dihydroisoxazole (3-a) Using Acid Catalyst

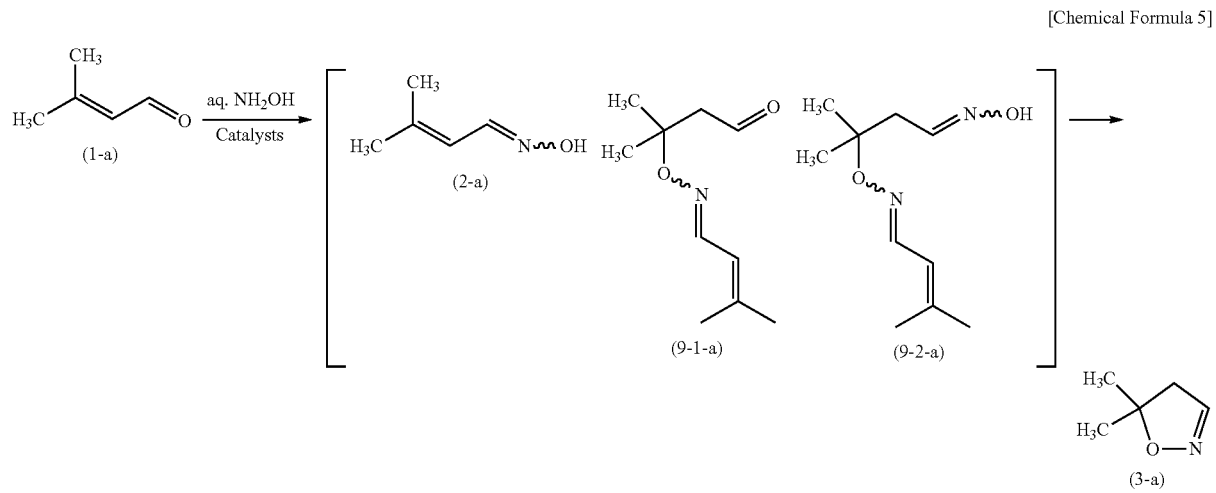

Prenal (478 μl, specific gravity: 0.879 (20° C.), 421 mg, purity: 98% (GC area %), 4.9 mmol, 100 mol %) was added to a 10 ml test tube with a cap using a microsyringe. Trifluoroacetic acid (38 μl, specific gravity: 1.49 (20° C.), 58 mg, 0.5 mmol, 10 mol %) was added thereto. A hydroxylamine aqueous solution (294 μl, specific gravity: 1.122 (20° C.), 330 mg, purity: 52% (titrated with 1.0 M hydrochloric acid), 5.19 mmol, 106 mol %) was added under ice-cooling such that the temperature did not exceed 30° C., followed by stirring (aging) at 30° C. for 24 hours. The reaction mixture was analyzed by GC (area percentage).

Examples 2 to 11

5,5-Dimethyl-4,5-dihydroisoxazole was produced in the same manner as in Example 1 except that the amount of hydroxylamine ($NH_2OH$), the type and the amount of the acid, and the stirring conditions (aging conditions) were changed as shown in the table below.

As a result of GC analysis (area percentage) of the reaction mixture, (1-a; raw material) and (3-a; target product) as well as (2-a; intermediate), (9-1-a; aldehyde derivative of dimeric intermediate) and (9-2-a; oxime derivative of dimeric intermediate) were detected as the components in the reaction mixture excluding the solvents and the like. In the present invention, (1-a; raw material), (3-a; target product), (2-a; intermediate), (9-1-a; aldehyde derivative of dimeric intermediate), and (9-2-a; oxime derivative of dimeric intermediate) were identified by analysis such as GC, GC-MS, and $^1$H NMR.

The results of GC analysis (area percentage) of the reaction mixtures of Examples 1 to 11 are shown in the table below.

| | $NH_2OH$ | Acid catalyst | | Stirring conditions (aging conditions) | | GC analysis (%) | | | | |
|---|---|---|---|---|---|---|---|---|---|---|
| Examples | mol % | Acid | mol % | Temperature (° C.) | Time (h) | (3-a) | (1-a) | (2-a) | (9-1-a) | (9-2-a) |
| 1 | 106 | TFA | 10 | 30 | 24 | 77 | 0 | 12 | 0 | 7 |
| 2 | 97 | TFA | 10 | 30 | 20 | 79 | 3 | 13 | 1 | 2 |
| 3 | 106 | TFA | 10 | 50 | 15 | 94 | 0 | 4 | 0 | 0 |
| 4 | 97 | TFA | 10 | 50 | 15 | 94 | 1 | 1 | 2 | 1 |
| 5 | 106 | TFA | 3 | 30 | 15 | 83 | 0 | 15 | 0 | 0 |
| 6 | 93 | TFA | 2 | 30 | 18 | 83 | 2 | 11 | 1 | 1 |
| 7 | 106 | Maleic acid | 10 | 30 | 24 | 81 | 0 | 13 | 0 | 4 |
| 8 | 106 | Maleic acid | 10 | 50 | 15 | 94 | 0 | 4 | 0 | 0 |
| 9 | 101 | Maleic acid | 10 | 50 | 7 | 90 | 0 | 5 | 1 | 2 |
| 10 | 102 | $NHO_3$ | 10 | 50 | 15 | 91 | 0 | 5 | 1 | 1 |
| 11 | 106 | TsOH | 5 | 30 | 15 | 81 | 0 | 12 | 0 | 3 |

Example 12

Production of 5,5-dimethyl-4,5-dihydroisoxazole (3-a) using acid catalyst in solvent containing organic solvent Prenal (478 µl, specific gravity: 0.879 (20° C.), 421 mg, purity: 98% (GC area %), 4.9 mmol, 100 mol %) was added to a 10 ml test tube with a cap using a microsyringe. Dichloromethane (0.5 ml, 0.1 L/mol) and trifluoroacetic acid (38 µl, specific gravity: 1.49 (20° C.), 58 mg, 0.5 mmol, 10 mol %) were added thereto. A hydroxylamine aqueous solution (282 µl, specific gravity: 1.122 (20° C.), 316 mg, purity: 52% (titrated with 1.0 M hydrochloric acid), 4.98 mmol, 102 mol %) was added under ice-cooling such that the temperature did not exceed 30° C., followed by stirring (aging) at 50° C. for 20 hours. The reaction mixture was analyzed by GC (area percentage).

Examples 13 to 15

5,5-Dimethyl-4,5-dihydroisoazole was produced in the same manner as in Example 12 except that the type and the amount of the solvent, the amount of hydroxylamine (NH$_2$OH), the type and the amount of the acid catalyst, and the stirring conditions (aging conditions) were changed as shown in the table below.

The results of GC analysis (area percentage) of the reaction mixtures of Examples 12 to 15 are shown in the table below.

Example 16

Production of 5,5-dimethyl-4,5-dihydroisoxazole (3-a) Using Acid-Base Catalyst Prenal (478 µl, specific gravity: 0.879 (20° C.), 421 mg, purity: 98% (GC area %), 4.9 mmol, 100 mol %) was added to a 10 ml test tube with a cap using a microsyringe. Trifluoroacetic acid (19 µl, specific gravity: 1.49 (20° C.), 29 mg, 0.25 mmol, 5 mol %) was added thereto. A hydroxylamine aqueous solution (268 µl, specific gravity: 1.122 (20° C.), 301 mg, purity: 52% (titrated with 1.0 M hydrochloric acid), 4.73 mmol, 97 mol %) was added under ice-cooling such that the temperature did not exceed 30° C., and then N-methylaniline (27 µl, specific gravity: 0.99 (20° C.), 27 mg, 0.25 mmol, 5 mol %) was added, followed by stirring (aging) at 30° C. for 20 hours. The reaction mixture was analyzed by GC (area percentage).

Examples 17 to 31

5,5-Dimethyl-4,5-dihydroisoxazole was produced in the same manner as in Example 16 except that the amount of hydroxylamine (NH$_2$OH), the type and the amount of the acid, the type and the amount of the base, and the stirring conditions (aging conditions) were changed as shown in the table below.

|  | Organic solvent | | NH$_2$OH | Acid catalyst | | Stirring conditions (aging conditions) | | GC analysis (%) | | | | |
|---|---|---|---|---|---|---|---|---|---|---|---|---|
| Examples | Organic solvent | L/mol | mol % | Acid | mol % | Temperature (° C.) | Time (h) | (3-a) | (1-a) | (2-a) | (9-1-a) | (9-2-a) |
| 12 | CH$_2$Cl$_2$ | 0.1 | 102 | TFA | 10 | 50 | 20 | 96 | 0 | 1 | 1 | 1 |
| 13 | CH$_2$Cl$_2$ | 0.2 | 101 | TFA | 10 | 50 | 15 | 96 | 0 | 0 | 1 | 1 |
| 14 | CH$_3$CN | 0.2 | 101 | TFA | 10 | 50 | 15 | 83 | 0 | 11 | 3 | 3 |
| 15 | t-BuOH | 0.2 | 101 | TFA | 10 | 50 | 15 | 91 | 0 | 4 | 1 | 1 |

NH$_2$OH: Hydroxylamine
TFA: Trifluoroacetic acid
CH$_2$Cl$_2$: Dichloromethane
CH$_3$CN: Acetonitrile
t-BuOH: tert-butanol

Comparative Example 1

5,5-Dimethyl-4,5-dihydroisoxazole was produced in the same manner as in Example 16 except that the amount of hydroxylamine (NH$_2$OH), the type and the amount of the base, and the stirring conditions (aging conditions) were changed as shown in the table below and the acid was not added.

The results of GC analysis (area percentage) of the reaction mixtures of Examples 16 to 31 and Comparative Example 1 are shown in the table below.

|  | NH$_2$OH | Acid-base catalyst | | | | Stirring conditions (aging conditions) | | GC analysis (%) | | | | |
|---|---|---|---|---|---|---|---|---|---|---|---|---|
| Examples | mol % | Acid | mol % | Base | mol % | Temperature (° C.) | Time (h) | (3-a) | (1-a) | (2-a) | (9-1-a) | (9-2-a) |
| 17 | 100 | TFA | 2 | PhNHMe | 2 | 30 | 20 | 77 | 0 | 12 | 2 | 6 |
| 18 | 98 | TFA | 2 | PhNHMe | 2 | 30 | 20 | 90 | 0 | 5 | 2 | 1 |
| 16 | 97 | TFA | 5 | PHNHMe | 5 | 30 | 20 | 94 | 0 | 1 | 2 | 0 |
| 19 | 97 | TFA | 10 | PhNHMe | 10 | 30 | 20 | 94 | 0 | 1 | 1 | 1 |
| 20 | 97 | TFA | 3 | PhNHMe | 2 | 30 | 20 | 94 | 0 | 2 | 1 | 0 |

-continued

| | NH$_2$OH | Acid-base catalyst | | | | Stirring conditions (aging conditions) | | GC analysis (%) | | | | |
|---|---|---|---|---|---|---|---|---|---|---|---|---|
| Examples | mol % | Acid | mol % | Base | mol % | Temperature (° C.) | Time (h) | (3-a) | (1-a) | (2-a) | (9-1-a) | (9-2-a) |
| 21 | 97 | TFA | 3 | PhNHMe | 1 | 30 | 20 | 93 | 1 | 3 | 1 | 0 |
| 22 | 93 | TFA | 2 | PhNHMe | 3 | 30 | 18 | 92 | 0 | 9 | 2 | 0 |
| 23 | 93 | TFA | 2 | PhNHMe | 2 | 30 | 18 | 90 | 1 | 6 | 1 | 0 |
| 24 | 93 | TFA | 2 | PhNHMe | 1 | 30 | 18 | 86 | 2 | 8 | 1 | 0 |
| 25 | 93 | TFA | 1 | PhNHMe | 1 | 30 | 18 | 77 | 2 | 12 | 2 | 5 |
| 26 | 97 | TFA | 5 | Morpholine | 5 | 30 | 20 | 72 | 1 | 17 | 2 | 6 |
| 27 | 97 | TFA | 5 | Pyrrolidine | 5 | 39 | 20 | 60 | 1 | 26 | 2 | 8 |
| 28 | 97 | Maleic acid | 3 | PhNHMe | 1 | 30 | 20 | 92 | 1 | 5 | 1 | 0 |
| 29 | 97 | HNO$_3$ | 3 | PhNHMe | 3 | 30 | 18 | 89 | 0 | 6 | 0 | 1 |
| 30 | 97 | HNO$_3$ | 3 | PhNHMe | 1 | 30 | 20 | 83 | 1 | 11 | 2 | 2 |
| 31 | 97 | TsOH | 3 | PhNHMe | 3 | 30 | 18 | 90 | 0 | 6 | 0 | 1 |
| Comparative Example 1 | 93 | — | 0 | PhNHMe | 2 | 30 | 18 | 23 | 2 | 39 | 7 | 27 |

NH$_2$OH: Hydroxylamine
TFA: Trifluoroacetic acid
PhNHMe: N-Methylaniline
TsOH: p-Toluenesulfonic acid monohydrate Examples 1 to 6 are examples in which an acid catalyst was used. When an acid catalyst was used, good yields were obtained under both conditions of prenal excess (Examples 2, 4, 6) and hydroxylamine excess (Examples 1, 3, 5). When an acid catalyst was used, there was obtained an effect that yield was not affected by the amount ratio (molar ratio) of prenal to hydroxylamine.

The results of Examples 7 to 11 show that various acids can be used as the acid catalyst of the present invention.

Examples 12 to 15 are examples in which an acid catalyst was used in a solvent containing an organic solvent. Good yields were obtained in the presence of various organic solvents.

Examples 16 to 25 are examples in which an acid-base catalyst was used. A good yield was obtained also in Example 17, in which an equal amount (in moles) of prenal and hydroxylamine were used. In particular, in Examples 16, and 18 to 23, in which the reaction was performed under the condition of prenal excess, better yields were obtained.

The results of Examples 26 to 31 show that various acids and bases can be utilized as the acid-base catalyst of the present invention.

Comparative Example 1 is an example in which the reaction was tried without any acid catalyst. The reaction hardly proceeded without any acid catalyst.

Reference Example 1

Production of 5,5-dimethyl-4,5-dihydroisoxazole (3-a)

Acetone oxime (326 mg, 4.45 mmol, 91 mol %) and prenal (478 μl, specific gravity: 0.879 (20° C.), 421 mg, purity: 98% (GC area %), 4.90 mmol, 100 mol %) were added to a 10 ml test tube with a cap. Water (147 mg, specific gravity: 1.00, 147 μl, 8.17 mmol, 167 mol %) was added thereto and ice-cooled. Trifluoroacetic acid (3.8 μl, specific gravity: 1.49 (20° C.), 5.7 mg, 0.050 mmol, 1 mol %) and N-methylaniline (5.4 μl, specific gravity: 0.99 (20° C.), 5.4 mg, 0.050 mmol, 1 mol %) were taken into the same gas tight syringe and mixed in the syringe. This mixture was added to the above test tube little by little in some portions such that the internal temperature did not exceed 20° C., followed by stirring (aging) at 30° C. for 20 hours. The GC analysis (area percentage) of the reaction mixture revealed that the main components in the reaction mixture excluding the solvent and the like were as follows; 5,5-dimethyl-4,5-dihydroisoxazole (3-a; target product): 37%, prenal (1-a; raw material): 29%, and acetone oxime (raw material): 17%.

In Reference Example 1, acetone oxime was used instead of hydroxylamine of the present invention. This corresponds to the process of Example 1 of Patent Document 2 being carried out in the presence of an amount of water contained in a 50% hydroxylamine aqueous solution in the same number of moles as acetone oxime used in Example 1 of JP 2013-512202 A (Patent Document 2).

The results of Reference Example 1 showed a clearly low yield. This result shows that, as expected from the description of Patent Document 2, the presence of water inhibits oximation and/or cyclization in the process of the Patent Document 2.

Although there was a difference in the behavior of the reaction intermediates detected during the reaction between the acid-catalyzed reaction and the acid-base-catalyzed reaction, the desired effect of the present invention was obtained even either with an acid catalyst or with an acid-base catalyst after the completion of the reaction as shown in the above table of Examples 1 to 31.

Meanwhile, the process using hydroxylamine of the present invention afforded a good yield despite the reaction in the presence of water, and therefore the process is suggested to be due to a reaction different from that of the process described in Patent Document 2.

Example 32

Production of 5,5-dimethyl-4,5-dihydroisoxazole (3-a)

Prenal (10.0 g, purity: 98% (GC area %), 116.5 mmol, 100 mol %) was dissolved in dichloromethane (11.7 ml, 0.1 L/mol) in a 50 ml round-bottom flask, and then trifluoroacetic acid (0.89 ml, specific gravity: 1.49 (20° C.), 1.33 g, 11.7 mmol, 10 mol %) was added under ice-cooling. A hydroxylamine aqueous solution (7.55 g, purity: 52% (titrated with 1.0 M hydrochloric acid), 118.8 mmol, 102 mol %) was added thereto under ice-cooling such that the temperature did not exceed 30° C., followed by stirring (aging) at 45° C. for 20 hours. The GC analysis (area percentage) of the reaction mixture revealed that the components in the reaction mixture excluding the solvents and the like were as follows; 5,5-dimethyl-4,5-dihydroisoxazole (3-a; target product): 96%.

After the completion of the reaction, a saturated sodium hydrogen carbonate aqueous solution (12 ml) was added, followed by stirring. The resultant mixture was partitioned between an organic layer and an aqueous layer. The organic layer and the aqueous layer were separated from each other. The aqueous layer was extracted with a small amount of dichloromethane, and the combined organic layer was concentrated under reduced pressure. The resultant crude product was purified by distillation under reduced pressure to obtain 5,5-dimethyl-4,5-dihydroisoxazole (3-a, colorless oil, 9.3 g, 93.8 mmol, yield: 81%, boiling point: 75 to 77° C./50 Torr).

Example 33

Production of 5,5-dimethyl-4,5-dihydroisoxazole (3-a)

Prenal (10.0 g, purity: 98% (GC area %), 116.5 mmol, 100 mol %) was dissolved in dichloromethane (11.7 ml, 0.1 L/mol) in a 50 ml round-bottom flask, and then maleic acid (1.35 g, 11.7 mmol, 10 mol %) was added under ice-cooling. A hydroxylamine aqueous solution (7.55 g, purity: 52% (titrated with 1.0 M hydrochloric acid), 118.8 mmol, 102 mol %) was added thereto under ice-cooling such that the temperature did not exceed 30° C., followed by stirring (aging) at 45° C. for 24 hours. The GC analysis (area percentage) of the reaction mixture revealed that the components in the reaction mixture excluding the solvents and the like were as follows; 5,5-dimethyl-4,5-dihydroisoxazole (3-a; target product): 97%.

After the completion of the reaction, a saturated sodium hydrogen carbonate aqueous solution (12 ml) was added, followed by stirring. The resultant mixture was partitioned between an organic layer and an aqueous layer. The organic layer and the aqueous layer were separated from each other. The aqueous layer was extracted with a small amount of dichloromethane, and the combined organic layer was concentrated under reduced pressure. The resultant crude product was purified by distillation under reduced pressure to obtain 5,5-dimethyl-4,5-dihydroisoxazole (3-a, colorless oil, 10.1 g, 101.9 mmol, yield: 87%, boiling point: 75 to 77° C./50 Torr).

Examples 34 and 35

5,5-Dimethyl-4,5-dihydroisoxazole was produced in the same manner as in Examples 32 and 33 except that the type and the amount of the solvent, the type of the catalyst, and the stirring conditions (aging conditions) were changed as shown in the table below. The results are shown in the table below.

Example 37

Production of 5,5-dimethyl-4,5-dihydroisoxazole (3-a)

Prenal (10.0 g, purity: 98% (GC area %), 116.5 mmol, 100 mol %) was added to a 50 ml round-bottom flask, and then trifluoroacetic acid (178 µl, specific gravity: 1.49 (20° C.), 266 mg, 2.33 mmol, 2 mol %) was added under ice-cooling. A hydroxylamine aqueous solution (7.25 g, purity: 52% (titrated with 1.0 M hydrochloric acid), 114.2 mmol, 98 mol %) was added thereto under ice-cooling such that the temperature did not exceed 30° C., and then N-methylaniline (252 µl, specific gravity: 0.99 (20° C.), 250 mg, 2.33 mmol, 2 mol %) was added, followed by stirring (aging) at 30° C. for 24 hours. The GC analysis (area percentage) of the reaction mixture revealed that the components in the reaction mixture excluding the solvents and the like were as follows; 5,5-dimethyl-4,5-dihydroisoxazole (3-a; target product): 96%.

After the completion of the reaction, dichloromethane (12 ml) and a saturated sodium hydrogen carbonate aqueous solution (12 ml) were added, followed by stirring. The resultant mixture was partitioned between an organic layer and an aqueous layer. The organic layer and the aqueous layer were separated from each other. The aqueous layer was extracted with a small amount of dichloromethane, and the combined organic layer was concentrated under reduced pressure. The resultant crude product was purified by distillation under reduced pressure to obtain 5,5-dimethyl-4,5-dihydroisoxazole (3-a, colorless oil, 9.7 g, 97.9 mmol, yield: 84%, boiling point: 75 to 77° C./50 Torr).

$^1$H-NMR (400 MHz, CDCl$_3$) δ (ppm, relative to TMS): 1.40 (s, 6H), 2.75 (d, J=1.9 Hz, 2H), 7.06 (s, 1H).

$^{13}$C-NMR (100 MHz, CDCl$_3$) δ (ppm): 27.0, 47.3, 82.2, 146.2.

Boiling point: 154.9° C./1 atm (TG-DTA: simultaneous thermogravimetry-differential thermal analysis). The following instrument was used for TG-DTA; Instrument: DSC 3100 S (manufactured by MAC Science Co., Ltd.).

Examples 36, 38, and 39

5,5-Dimethyl-4,5-dihydroisoxazole was produced in the same manner as in Example 37 except that the type and the amount of the catalyst, and the stirring conditions (aging conditions) were changed as shown in the table below.

The results of Examples 32 to 39 are shown in the table below.

| | Organic solvent | | NH$_2$OH | Catalyst | | | | Stirring conditions (aging conditions) | | Reaction mixture GC analysis (%) | Isolated yield (%) |
|---|---|---|---|---|---|---|---|---|---|---|---|
| Examples | Organic solvent | L/mol | mol % | Acid | mol % | Base | mol % | Temperature (° C.) | Time (h) | (3-a) | (3-a) |
| 32 | CH$_2$Cl$_2$ | 0.1 | 102 | TFA | 10 | None | 0 | 45 | 20 | 96 | 81 |
| 33 | CH$_2$Cl$_2$ | 0.1 | 102 | Maleic acid | 10 | None | 0 | 45 | 24 | 97 | 87 |

-continued

| | Organic solvent | | NH$_2$OH | Catalyst | | | | Stirring conditions (aging conditions) | | Reaction mixture GC analysis (%) | Isolated yield (%) |
|---|---|---|---|---|---|---|---|---|---|---|---|
| Examples | Organic solvent | L/mol | mol % | Acid | mol % | Base | mol % | Temperature (° C.) | Time (h) | (3-a) | (3-a) |
| 34 | Cyclohexane | 0.1 | 102 | Maleic acid | 10 | None | 0 | 45 | 24 | 97 | 74 |
| 35 | CH$_2$Cl$_2$ | 0.1 | 102 | HNO$_3$ | 10 | None | 0 | 45 | 24 | 95 | 79 |
| 36 | None | 0 | 102 | TFA | 10 | None | 0 | 50 | 24 | 94 | 75 |
| 37 | None | 0 | 98 | TFA | 2 | PhNHMe | 2 | 30 | 24 | 98 | 84 |
| 38 | None | 0 | 98 | Maleic Acid | 3 | PhNHMe | 1 | 30 | 48 | 93 | 85 |
| 39 | None | 0 | 98 | HNO$_3$ | 3 | PhNHMe | 3 | 30 | 48 | 96 | 84 |

NH$_2$OH: Hydroxylamine
TFA: Trifluoroacetic acid
PhNHMe: N-Methylaniline
CH$_2$Cl$_2$: Dichloromethane Example 40

Production of 5,5-dimethyl-4,5-dihydroisoxazole (3-a) Using Hydroxylamine Hydrochloride and Acid Catalyst Prenal (10.0 g, purity: 98% (GC area %), 116.5 mmol, 100 mol %) was dissolved in dichloromethane (11.7 ml, 0.1 L/mol) in a 100 ml round-bottom flask, and then trifluoroacetic acid (0.89 ml, specific gravity: 1.49 (20° C.), 1.33 g, 11.7 mmol, 10 mol %) and hydroxylamine hydrochloride (8.26 g, 118.8 mmol, 102 mol %) were added under ice-cooling. A 48% sodium hydroxide aqueous solution (9.90 g, 118.8 mmol, 102 mol %) was added thereto under ice-cooling such that the temperature did not exceed 30° C., followed by stirring (aging) at 45° C. for 20 hours. The GC analysis (area percentage) of the reaction mixture revealed that the components in the reaction mixture excluding the solvents and the like were as follows; 5,5-dimethyl-4,5-dihydroisoxazole (3-a; target product): 92%.

After the completion of the reaction, a saturated sodium hydrogen carbonate aqueous solution (12 ml) was added, followed by stirring. The resultant mixture was partitioned between an organic layer and an aqueous layer. The organic layer and the aqueous layer were separated from each other. The aqueous layer was extracted with a small amount of dichloromethane, and the combined organic layer was concentrated under reduced pressure. The resultant crude product was purified by distillation under reduced pressure to obtain 5,5-dimethyl-4,5-dihydroisoxazole (3-a, colorless oil, 8.8 g, 88.6 mmol, yield: 76%, boiling point: 75 to 77° C./50 Torr).

Example 41

Production of 5,5-dimethyl-4,5-dihydroisoxazole (3-a) Using Hydroxylamine Hydrochloride and Acid-Base Catalyst Prenal (10.0 g, purity: 98% (GC area %), 116.5 mmol, 100 mol %) was dissolved in dichloromethane (11.7 ml, 0.1 L/mol) in a 100 ml round-bottom flask, and then trifluoroacetic acid (178 µl, specific gravity: 1.49 (20° C.), 266 mg, 2.33 mmol, 2 mol %) and hydroxylamine hydrochloride (7.91 g, 113.9 mmol, 98 mol %) were added under ice-cooling. A 48% sodium hydroxide aqueous solution (9.49 g, 113.9 mmol, 98 mol %) was added thereto under ice-cooling such that the temperature did not exceed 30° C. Then, N-methylaniline (252 µl, specific gravity: 0.99 (20° C.), 250 mg, 2.33 mmol, 2 mol %) was added, followed by stirring at 30° C. for 5 hours. Then, trifluoroacetic acid (178 µl, specific gravity: 1.49 (20° C.), 266 mg, 2.33 mmol, 2 mol %) and N-methylaniline (252 µl, specific gravity: 0.99 (20° C.), 250 mg, 2.33 mmol, 2 mol %) were additionally added, followed by stirring (aging) at 30° C. for 24 hours. The GC analysis (area percentage) of the reaction mixture revealed that the components in the reaction mixture excluding the solvents and the like were as follows; 5,5-dimethyl-4,5-dihydroisoxazole (3-a; target product): 89%.

After the completion of the reaction, a saturated sodium hydrogen carbonate aqueous solution (12 ml) and water (20 ml) were added, followed by stirring. The resultant mixture was partitioned between an organic layer and an aqueous layer. The organic layer and the aqueous layer were separated from each other. The aqueous layer was extracted with a small amount of dichloromethane, and the combined organic layer was concentrated under reduced pressure. The resultant crude product was purified by distillation under reduced pressure to obtain 5,5-dimethyl-4,5-dihydroisoxazole (3-a, colorless oil, 8.6 g, 87.0 mmol, yield: 75%, boiling point: 75 to 77° C./50 Torr).

Example 42

Production of 5,5-dimethyl-4,5-dihydroisoxazole (3-a) Using Hydroxylamine Sulfate and Acid Catalyst Prenal (10.0 g, purity: 98% (GC area %), 116.5 mmol, 100 mol %) was dissolved in dichloromethane (11.7 ml, 0.1 L/mol) in a 100 ml round-bottom flask, and then hydroxylamine sulfate (9.75 g, 59.4 mmol, 51 mol %, 102 mol % in terms of hydroxylamine (NH$_2$OH)) was added. A 48% sodium hydroxide aqueous solution (9.22 g, 110.7 mmol, 95 mol %) was added thereto at 15 to 25° C., and then trifluoroacetic acid (2.68 ml, specific gravity: 1.49 (20° C.), 3.99 g, 34.9 mmol, 30 mol %) was added under ice-cooling, followed by stirring (aging) at 45° C. for 20 hours. The GC analysis (area percentage) of the reaction mixture revealed that the components in the reaction mixture excluding the solvents and the like were as follows; 5,5-dimethyl-4,5-dihydroisoxazole (3-a; target product): 92%.

After the completion of the reaction, a saturated sodium hydrogen carbonate aqueous solution (12 ml) was added, followed by stirring. Suction filtration was performed to remove the precipitated solid matter. After the filtration, the resultant mixture was partitioned between an organic layer and an aqueous layer. The organic layer and the aqueous layer were separated from each other. The aqueous layer was extracted with a small amount of dichloromethane and the organic layers were combined. GC analysis using 1,4-diphenoxybenzene as an internal standard revealed that the yield of 5,5-dimethyl-4,5-dihydroisoxazole (3-a; the desired product) was 79%.

The combined organic layer was concentrated under reduced pressure. The resultant crude product was purified by distillation under reduced pressure to obtain 5,5-dimethyl-4,5-dihydroisoxazole (3-a, colorless oil, 8.22 g, 82.9 mmol, yield: 71%, boiling point: 75 to 77° C./50 Torr).

The results of Examples 40 to 42 are shown in the table below.

| | Organic solvent | | $NH_2OH$ | | | Catalyst | | | Stirring conditions (aging conditions) | | Reaction mixtire GC analysis (%) | Isolated yield (%) |
|---|---|---|---|---|---|---|---|---|---|---|---|---|
| Examples | Organic solvent | L/mol | Salt | mol % (as $NH_2OH$) | Acid | mol % | Base | mol % | Temperature (° C.) | Time (hr) | (3-a) | (3-a) |
| 40 | $CH_2Cl_2$ | 0.1 | $NH_2OH \cdot HCl$ | 102 | TFA | 10 | None | 0 | 45 | 20 | 92 | 76 |
| 41 | $CH_2Cl_2$ | 0.1 | $NH_2OH \cdot HCl$ | 98 | TFA | 4 | PhNHMe | 4 | 30 | 30 | 89 | 75 |
| 42 | $CH_2Cl_2$ | 0.1 | $(HONH_2)_2 \cdot H_2SO_4$ | 102 | TFA | 30 | None | 0 | 45 | 20 | 92 | 71 |

$NH_2OH$: Hydroxylamine
$CH_2Cl_2$: Dichloromethane
$NH_2OH \cdot HCl$: Hydroxylamine hydrochloride
$(HONH_2)_2 \cdot H_2SO_4$: Hydroxylamine sulfate
TFA: Trifluoroacetic acid
PhNHMe: N-Methylaniline

INDUSTRIAL APPLICABILITY

The 5,5-disubstituted-4,5-dihydroisoxazole of the formula (3) produced by the process of the present invention is useful as an intermediate for producing pharmaceutical and agricultural chemicals etc., particularly, a herbicide pyroxasulfone. According to the present invention, the generation of by-products and/or wastes can be suppressed, and atom efficiency can be improved. Furthermore, according to the present invention, the target compound can be efficiently produced by a safe and simple operation. Therefore, the process of the present invention is safe, industrially preferable, economical, and environmentally friendly, and has high industrial utility value. In short, the present invention has high industrial applicability.

The invention claimed is:

1. A process for producing a compound of the formula (3), comprising reacting a compound of the formula (1) with hydroxylamine in the presence of a catalyst:

[Chemical Formula 1]

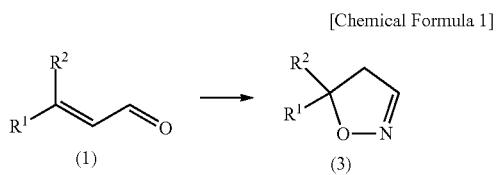

in the formula (3), $R^1$ and $R^2$ are each independently an optionally substituted (C1-C6)alkyl; an optionally substituted (C3-C6)cycloalkyl; an optionally substituted (C2-C6)alkenyl; an optionally substituted (C2-C6)alkynyl; an optionally substituted (C1-C6)alkoxy; or an optionally substituted phenyl; or $R^1$ and $R^2$, together with the carbon atom to which they are attached form a 4- to 12-membered carbocyclic ring, wherein the formed ring is optionally substituted, in the formula (1), $R^1$ and $R^2$ are as defined above.

2. The process according to claim 1, wherein the reaction of the compound of the formula (1) with hydroxylamine is performed in the presence of water.

3. The process according to claim 1, wherein the reaction of the compound of the formula (1) with hydroxylamine is performed in the presence of 100 mol % or more of water based on 1 mol of the compound of the formula (1).

4. The process according to claim 1, wherein the reaction of the compound of the formula (1) with hydroxylamine is performed in the presence of 100 mol % to 1000 mol % of water based on 1 mol of the compound of the formula (1).

5. The process according to claim 1, wherein the catalyst is an acid catalyst.

6. The process according to claim 5, wherein the acid catalyst is one or more acids selected from the group consisting of mineral acids, carboxylic acids, and sulfonic acids.

7. The process according to claim 5, wherein the acid catalyst is one or more acids selected from the group consisting of nitric acid, trifluoroacetic acid, maleic acid, and p-toluenesulfonic acid.

8. The process according to claim 5, wherein the acid catalyst is trifluoroacetic acid.

9. The process according to claim 1, wherein the catalyst is an acid-base catalyst.

10. The process according to claim 9, wherein the acid of the acid-base catalyst is one or more acids selected from the group consisting of mineral acids, carboxylic acids, and sulfonic acids.

11. The process according to claim 9, wherein the acid of the acid-base catalyst is one or more acids selected from the group consisting of nitric acid, trifluoroacetic acid, maleic acid, and p-toluenesulfonic acid.

12. The process according to claim 9, wherein the acid of the acid-base catalyst is trifluoroacetic acid.

13. The process according to claim 9, wherein the base of the acid-base catalyst is one or more bases selected from the group consisting of N-methylaniline, morpholine, and pyrrolidine.

14. The process according to claim 9, wherein the base of the acid-base catalyst is N-methylaniline.

15. The process according to claim 1, wherein the hydroxylamine is a free hydroxylamine aqueous solution or a hydroxylamine salt.

16. The process according to claim 1, wherein the hydroxylamine is a 45% to 55% hydroxylamine aqueous solution, hydroxylamine hydrochloride, or hydroxylamine sulfate.

17. The process according to claim 1, wherein the hydroxylamine is a hydroxylamine salt, and the reaction is performed in the further presence of a neutralizing agent.

18. The process according to claim 1, wherein the hydroxylamine is hydroxylamine hydrochloride or hydroxylamine sulfate, and the reaction is performed in the further presence of a neutralizing agent.

19. The process according to claim 17, wherein the neutralizing agent is sodium hydroxide, potassium hydroxide, sodium carbonate, potassium carbonate, sodium hydrogen carbonate, potassium hydrogen carbonate, or ammonia.

20. The process according to claim 1, wherein the reaction is performed in the presence of one or more solvents selected from acetonitrile, toluene, xylene, chlorobenzene, dichlorobenzene, and dichloromethane, and a water solvent.

21. The process according to claim 1, wherein the reaction is performed in the presence of a solvent composed of a combination of water and dichlorobenzene.

22. The process according to claim 1, wherein the compound of the formula (1) is prenal and the compound of the formula (3) is 5,5-dimethyl-4,5-dihydroisoxazole.

* * * * *